United States Patent [19]

Altman et al.

[11] Patent Number: 5,572,421

[45] Date of Patent: Nov. 5, 1996

[54] PORTABLE MEDICAL QUESTIONNAIRE PRESENTATION DEVICE

[76] Inventors: Louis Altman; David Summerell, both of 5622 S. Woodlawn, Chicago, Ill. 60637; William E. Turcotte, II, 1234 Edmer St., Oak Park, Ill. 60302

[21] Appl. No.: 253,201

[22] Filed: Jun. 2, 1994

Related U.S. Application Data

[63] Continuation of Ser. No. 711,616, Jun. 6, 1991, abandoned, which is a continuation-in-part of Ser. No. 130,934, Dec. 9, 1987, Pat. No. 5,025,374.

[51] Int. Cl.⁶ .................................................. G06F 159/00
[52] U.S. Cl. ............................................ 395/203; 395/202
[58] Field of Search ........................ 364/413.01, 413.02; 395/401, 924

[56] References Cited

U.S. PATENT DOCUMENTS

| | | | |
|---|---|---|---|
| 3,566,370 | 2/1971 | Worthington | 364/413.01 |
| 3,934,226 | 1/1976 | Stone | 364/413.01 |
| 4,130,881 | 12/1978 | Haessler et al. | 364/413.01 |
| 4,365,315 | 12/1982 | Jamnik | 364/419 |
| 4,545,023 | 10/1985 | Mizzi | 364/709 |
| 4,680,731 | 7/1987 | Izumi et al. | 364/479 |

OTHER PUBLICATIONS

"Medical Progress, Decision Analysis", The New England Jnl of Med. Jan. 29, 1987, Stephen G. Pauker et al.
"Graphical Access To Medical Expert Systems: II: Design Interface For Physicians", C. D. Lane, Methods of Inf. In Med.: 25:143–150, 1986.
"A Decision–Driven System To Collect Patient History", Computers And Biomedical Research, 20 193–207(1987).
"Oncocin: An Expert System For Oncology Protocol Management", Edward H. Shortliffepro: of 7th Int. Jnl Conf. on A. I., Vancouver BC Aug./1981.
A. W. Grogono, "Index For Measuring Health", The Lancet, Nov. 6, 1971 pp. 1024–1026.
"Sickness Impact Profile", John Hopkins University 1977, 21 pages.

*Primary Examiner*—Robert A. Weinhardt
*Attorney, Agent, or Firm*—Laff, Whitesel, Conte & Saret, Ltd.

[57] ABSTRACT

A hand-held, battery-powered medical questionnaire presentation device is provided for use by a patient. The device has means for displaying questions to the patient, a limited number of keys by which the patient can enter answers, and a memory device for storing the patient's answers. The device is controlled by a pre-programmed microcomputer which stores in a memory the text of user instructions, medical or health-related questions, and words to be used in printed reports. The microcomputer is programmed to tally the patient's answers and, on the basis of that information and objective data supplied by a medical staffer, to present an evaluation of aspects of the patient's medical condition or health status. The evaluation may consist of recommendations for tests, an analysis of the patient's general medical condition, an analysis of the patient's surgical risk, an analysis of the patient's functional health status, recommendations for counseling the patient, recommendations for health-related lifestyle improvements, or any other conclusions which may be inferred from the patient's responses. The questions and the answer-evaluation software are stored in a readily removable and replaceable integrated circuit module. A variety of specialized questionnaires targeting particular health risks and medical conditions may be provided on interchangeable modules.

8 Claims, 27 Drawing Sheets

Microfiche Appendix Included
(3 Microfiche, 256 Pages)

```
┌─────────────────────────────────────────────┐
│  ┌───────────────────────────────────────┐  │
│  │ HAVE YOU TAKEN ASPRIN, EXCEDRIN, ANACIN,│  │
│  │ BUFFERIN, ALKASELTZER OR ANY SIMILAR  │  │
│  │ MEDICATIONS IN THE LAST WEEK?         │  │
│  │                           NOT SURE    │  │
│  └───────────────────────────────────────┘  │
│                                       ╲ 22  │
│   ┌─ ─ ─ ─ ─ ─┐                              │
│   ╎  ╎  ╎  ╎  ╎    ┌───┐┌──┐┌────┐┌─────┐   │
│   ├─ ┼─ ┼─ ┼─ ┤    │YES││NO││N.S.││NEXT │   │
│   ╎  ╎  ╎  ╎  ╎    └───┘└──┘└────┘│QUES.│   │
│   ├─ ┼─ ┼─ ┼─ ┤                   └─────┘   │
│   ╎  ╎  ╎  ╎ #╎        ANSWER BUTTONS       │
│   └─ ─ ─ ─ ─ ─┘                              │
└──╱──────────────────────────────────────────┘
  36′            FIG. 3D
```

```
┌─────────────────────────────────────────────┐
│  ┌───────────────────────────────────────┐  │
│  │   THIS COMPLETES THE QUESTIONNAIRE.   │  │
│  │      THANK YOU FOR YOUR TIME.         │  │
│  │  PLEASE RETURN THIS UNIT FOR ANALYSIS.│  │
│  └───────────────────────────────────────┘  │
│                                       ╲ 22  │
│   ┌─ ─ ─ ─ ─ ─┐                              │
│   ╎  ╎  ╎  ╎  ╎    ┌───┐┌──┐┌────┐┌─────┐   │
│   ├─ ┼─ ┼─ ┼─ ┤    │YES││NO││N.S.││NEXT │   │
│   ╎  ╎  ╎  ╎  ╎    └───┘└──┘└────┘│QUES.│   │
│   ├─ ┼─ ┼─ ┼─ ┤                   └─────┘   │
│   ╎  ╎  ╎ # ╎         ANSWER BUTTONS        │
│   └─ ─ ─ ─ ─ ─┘                              │
└──╱──────────────────────────────────────────┘
  36′            FIG. 3E
```

```
┌─────────────────────────────────────────────┐
│  ┌───────────────────────────────────────┐  │
│  │        QUESTIONAIRE COMPLETED         │  │
│  │          ENTER ACCESS CODE            │  │
│  │                XXXX                   │  │
│  └───────────────────────────────────────┘  │
│                                       ╲ 22  │
│   ┌──┬──┬──┐                                 │
│   │ 1│ 2│ 3│       ┌───┐┌──┐┌────┐┌─────┐   │
│   ├──┼──┼──┤       │YES││NO││N.S.││NEXT │   │
│   │ 4│ 5│ 6│       └───┘└──┘└────┘│QUES.│   │
│   ├──┼──┼──┤                      └─────┘   │
│   │ 7│ 8│ 9│          ANSWER BUTTONS        │
│   ├──┼──┼──┤                                 │
│   │ *│ 0│ #│                                 │
│   └──┴──┴──┘                                 │
└──╱──────────────────────────────────────────┘
  36′            FIG. 3F
```

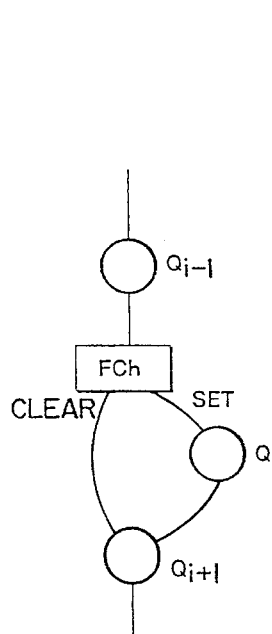
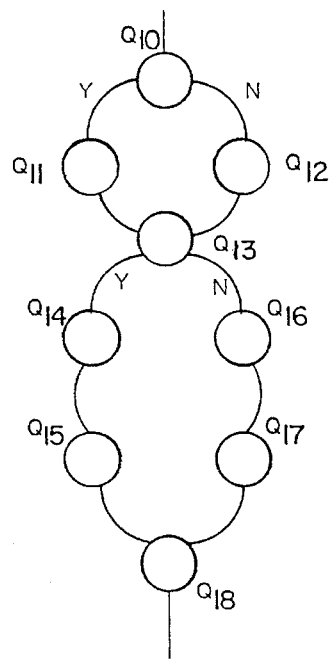
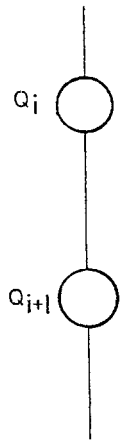
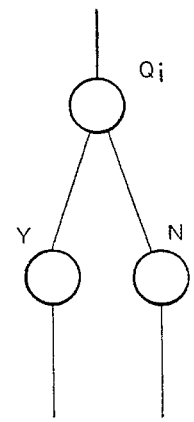
FIG. 13A  FIG. 13B  FIG. 13C  FIG. 13D
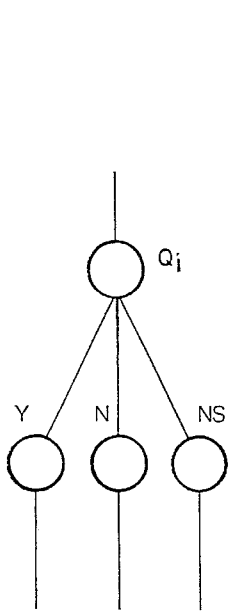
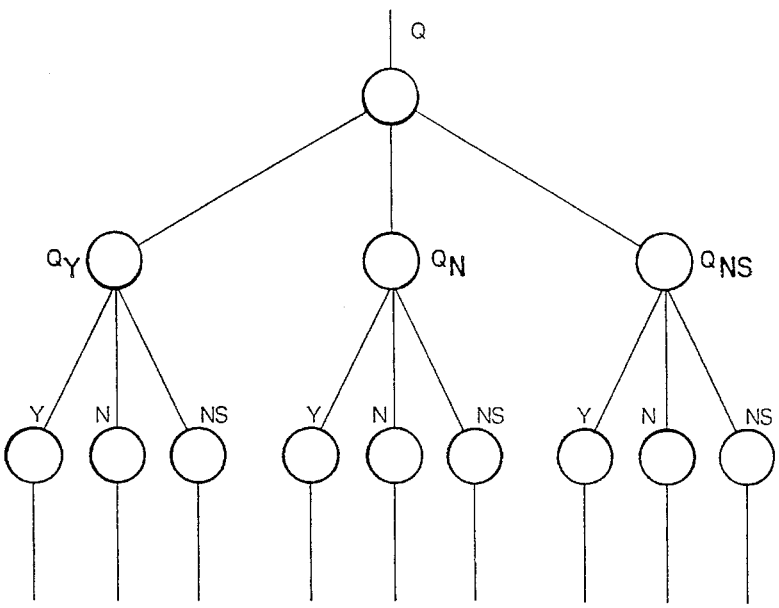
FIG. 13E  FIG. 13F

PORTABLE MEDICAL QUESTIONNAIRE PRESENTATION DEVICE

This application is a continuation, of application Ser. No. 07/711,616 filed Jun. 6, 1991 now abandoned, which in turn is a continuation-in-part of Ser. No. 07/130,934 filed Dec. 9, 1987, now U.S. Pat. No. 5,025,374.

REFERENCE TO MICROFICHE APPENDIX

A microfiche appendix to this patent application, comprising three sheets of microfiche, contains 256 frames of computer program listings illustrating a preferred embodiment of the computer software code contemplated by the invention disclosed below.

BACKGROUND OF THE INVENTION

This invention relates to a device for administering a medical questionnaire, and more particularly to a portable computerized device which administers a questionnaire to a patient, even if the patient is bed-ridden, and is capable of printing out a full report of the information obtained using the questionnaire, including advice to the physician concerning the patient's health status, indicated pre-operative or other medical tests, an assessment of the patient's risk in undergoing certain medical procedures, suggestions concerning the health effects of the patient's lifestyle, and other health-related information.

It has been estimated that of the approximately $30 billion spent each year in the United States for medical tests, as much as 60% of that amount ($18 billion) is wasted on unnecessary tests; i.e., those which, for a given patient, would not be needed if the physician had the benefit of a reliable medical history. See, for example, *Are We Hooked on Tests*, U.S. News & World Report, Nov. 23, 1987, pp. 60–65, 68–70, 72.

This problem of unnecessary testing is particularly acute in cases where a patient is about to undergo surgery and, in order to determine the proper anesthesia, the patient's general medical history is taken.

This medical history strongly influences which diagnostic tests the medical staff chooses to perform before surgery. For example, if the patient discloses that he or she has any pain or discomfort upon urination, or has noticed any blood in the urine, then a urinalysis (a chemical analysis of the urine) ought to be performed. But if those symptoms are not present, it is considered medically unnecessary to administer a urinalysis, absent some other medical indication for the test.

Under current medical practice, it requires about seventy-five or more questions to determine which, if any, of the various available pre-operative tests (urinalysis, chest x-rays, EKG, etc.) might have to be performed before determining what anesthesia ought to be used during surgery. If the physician is not sure that all these questions were properly asked, or has doubts about the care with which the patient's answers have been recorded, he or she is likely to include in the battery of pre-operative tests many that could have been excluded based on an accurate patient history.

To save the time of physicians, questionnaires have been devised that can be administered by a nurse or other trained medical worker, or even directly filled in by the patient. But the time of a trained medical worker is also too valuable to spend on such tasks, since that makes the individual unavailable to perform other, more pressing, medical tasks which require such training.

If the patient completes the questionnaire alone, he or she may overlook or ignore some of the questions. Also, if the patient usually reads in a foreign language or has vision problems, he or she may have trouble completing the questionnaire alone.

Even if a questionnaire is fully and properly filled out, tallying of the patient's answers to determine which tests are needed is a time-consuming and tedious task, in the course of which medical workers sometimes inadvertently introduce errors.

Because of these problems, all too often a reliable medical history of this type is not taken prior to surgery, in which case the patient may have to undergo a comprehensive battery of pre-operative tests, many of them unneeded. These unnecessary tests are expensive for the patient and a burden on an already overworked medical system. In addition, the more tests are done the greater is the risk of false positives and iatrogenic harm from pursuit of false positives. Therefore, there is a great need to "automate" the reliable taking and tabulating of pre-operative test questionnaires.

However, the need for accurate, extensive information as to a patient's current and previous medical status is not limited to situations in which the patient is about to undergo surgical procedures. For example, an extensive inquiry into a patient's medical history and current health is useful in developing an appropriate plan of preventive health care. Where a patient may be a member of a group at high risk for certain types of disease, an extensive inquiry concerning symptoms and lifestyle characteristics associated with the causes or symptoms of those diseases aids the physician in detecting and treating them.

Severe time constraints may prevent physicians from directly soliciting this information from the patient, and patients may be unwilling to disclose certain details about their medical conditions to medical personnel who are not physicians. Hence, existing schemes for soliciting detailed medical condition information from a patient may not reveal important clues concerning health conditions for which the patient may be at risk.

In addition, in many medical disciplines, it is desirable to derive, from information obtained from the patient, a numerical measure of the patient's health risk, surgical risk, capacity to function in daily life, or the like. The numerical measure permits the patient's performance or medical condition to be more easily compared with those of other patients. At present, the raw data required to calculate these numerical measures are abstracted from the patient's medical history, and the measure is calculated, by clerical personnel. This process is time-consuming and expensive, and is susceptible to human error. Accordingly, there is a significant need to automate the data collection and calculations required to produce these numerical measures.

It is also often desirable for the physician to counsel the patient concerning lifestyle changes which may help to improve the patient's health or reduce health risk. Because the physician is under severe time constraints, his or her attention may be primarily directed to the patient's current medical problems. Accordingly, the need exists for means to automatically remind the physician of lifestyle counseling which may be indicated by the health-related information obtained from the patient.

THE PRIOR ART

The prior art has proposed the use of computers or computer terminals to automate the taking of general-purpose medical histories. For example, in U.S. Pat. No. 3,566,370 of Worthington et al. a computer terminal which is connected by telephone lines to a mainframe computer displays questions on a CRT screen which are to be answered by the patient sitting at a full alphanumeric keyboard. After the patient answers the questions, the computer stores, formats and prints out the patient's medical history. The Worthington patent also suggests that the questions presented to the patient for the purpose of taking his medical history can be in foreign languages when necessary. U.S. Pat. No. 4,130,881 of Haessler et al. is similar to Worthington in many respects.

Published Japanese Patent Application No. 59-231676 is similar to the above-mentioned U.S. patents in its use of a computer console and full alphanumeric keyboard, except that in addition the computer there is programmed to develop recommendations. The recommendations are intended for the guidance of Japanese pharmacists, not medically trained physicians, in prescribing oral medications according to Chinese traditional folk medicine criteria. To date no computerized system has been developed which is specifically programmed to administer the particular sequence of questions which is considered appropriate for pre-operative test selection according to accepted western scientific medical criteria.

General-purpose computing machines of the type employed in the above prior art patents are much too expensive, bulky, and complicated for the task of automating the pre-operative test selection process. Moreover, the great majority of patients are not "computer literate" and find such equipment difficult to use even when they are feeling well. A patient who is about to go into surgery in the very near future is particularly likely to find a large-scale general-purpose computer system confusing and threatening. The problem is exacerbated by the fact that these computers require the patient to compose an answer on a keyboard containing the full range of alphanumeric characters and other keys.

The prior art has recognized the need in certain contexts for a simplified special-purpose data-processing device which offers the non-computer-literate person a simple choice between "yes" and "no" answers, as in published French Patent Application No. 77 17048. But the computer in that application is programmed to recommend a skin cosmetic regime rather than a medical treatment procedure.

A pre-operative patient is sometimes in such poor condition that it would be physically difficult to get out of bed and sit at the keyboard of large-scale computer system. Ideally, therefore, an automated pre-operative test recommendation device would be small enough to be portable. Here again, the prior art does have examples of portable special-purpose computers, but these too have not been adapted for use in a pre-operative test selection environment, or in other health-related environments in which the physical abilities of the patient may be substantially impaired. The portable computer in U.S. Pat. No. 4,686,624 of Blum et al., for example, is dedicated to controlling the dietary habits of diabetics.

OBJECTS AND SUMMARY OF THE INVENTION

Accordingly, one general object of the invention is to provide an automatic device for taking patient histories which is especially adapted for the selection of medical and/or pre-operative tests, and can be easily used even by bed-ridden patients.

Another general object of the invention is to provide an automatic device for presenting to patients a variety of health-related questionnaires which can be easily used even by bed-ridden patients.

A more particular object is to provide a small, battery-powered, portable dedicated computer that automatically displays questions and enables a non-computer-literate patient to answer by means of only a few keys.

A further object is to provide such a device that automatically analyzes the patient's answers to determine which tests appear to be necessary, and provides a printed report.

Another object is to provide a device that automatically analyzes the patient's answers to draw and report other health-related inferences, numerical measures of the patient's current health status, surgical risk, ability to function in daily life, need for lifestyle counseling, and the like.

Yet another object is to provide a device which is medically reliable, but is nevertheless relatively inexpensive.

It is also desirable to provide a device of this type which can be easily be field-modified to update the questions at intervals to keep up with the progress of medical knowledge.

Such a device should also be capable of communicating with either the patient or the doctor in a foreign language when necessary.

The invention provides a hand-held, battery-powered medical questionnaire presentation device for use by a patient which has means for displaying questions to a patient, a limited number of keys by which the patient can enter answers, and a memory device for storing the patient's answers. Alternatively, an audio jack enables the patient to listen to the questions with earphones. The device preferably uses a low-power display such as a liquid crystal or the like. In a preferred embodiment, no more than four keys are used by the patient: YES, NO, NOT SURE, and GO TO NEXT QUESTION. Additional control keys may be provided for use by the medical staff, but are hidden from the patient. The device is controlled by a pre-programmed microcomputer which stores in a memory the text of user instructions, medical or health-related questions, and words to be used in printed reports.

The microcomputer is programmed to tally the patient's answers and, on the basis of that information and objective data entered by a medical staffer, to present an evaluation of aspects of the patient's medical condition or health status. The evaluation may consist of recommendations for medical tests, an analysis of the patient's general medical condition, an analysis of the patient's surgical risk, recommendations for health-related lifestyle improvements, recommendations for patient counselling, recommended physical examination, recommendations for patient immunization, or any other similar information which may be inferred from the patient's responses. The presentation device can be provided with additional prestored text so the user has the option of displaying questions in more than one language, or being asked the questions in an audio mode. The questions and the answer-evaluation software are stored in a readily removable and replaceable integrated circuit module to facilitate updating of the questions and/or the test selection procedure at intervals, as medical knowledge advances. In addition, a variety of specialized questionnaires targeting particular health risks and medical conditions may be provided on interchangeable modules.

BRIEF DESCRIPTION OF THE DRAWINGS

These and other features of the invention will become more apparent, and the operation of the invention will be best understood, by reference to the following detailed description of preferred embodiments of the invention, when taken in conjunction with the accompanying drawings, in which:

FIGS. 3A–3F are views of the display and control keys of the questionnaire presentation device when it is in various modes of operation;

FIGS. 13A–13F show nodes representing questions to be asked and various arrangements of program paths linking the questions;

DETAILED DESCRIPTION OF THE PREFERRED EMBODIMENT

1. GENERAL APPEARANCE AND FUNCTIONS

Figure 1:
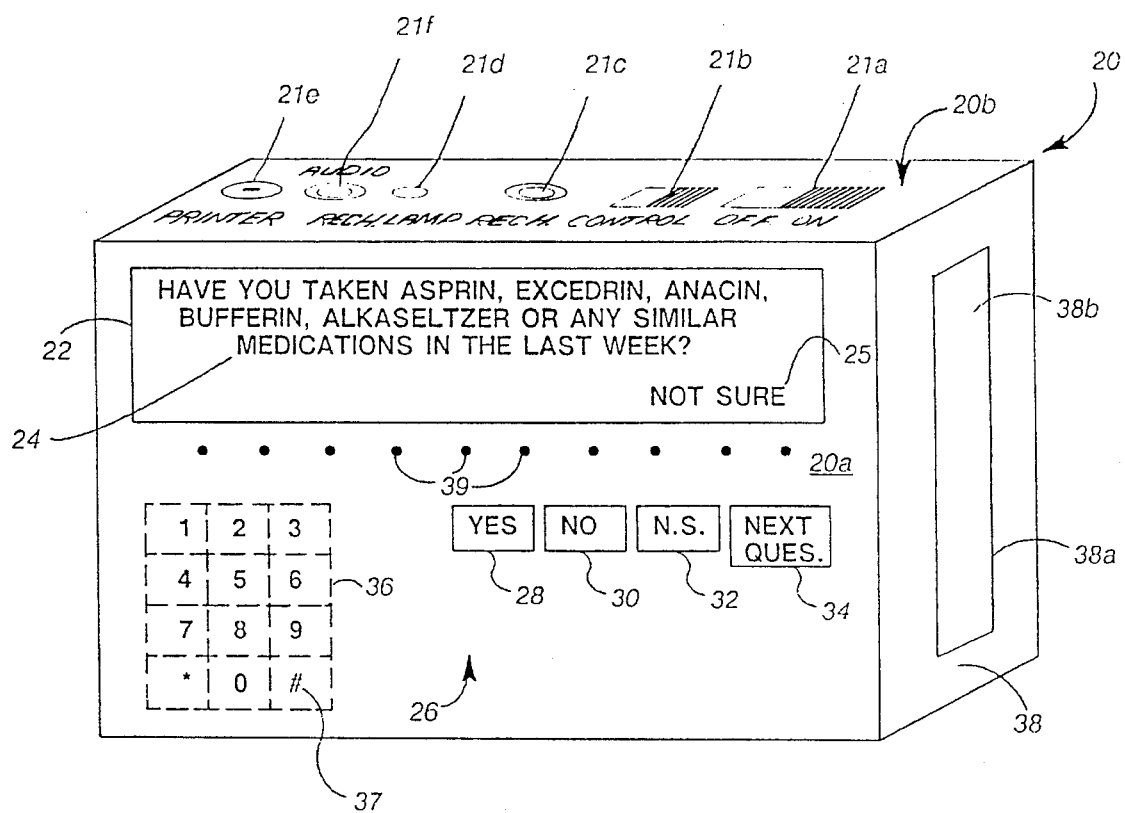
FIG. 1 is perspective view of an exemplary medical questionnaire presentation device constructed according to the invention.

A portable interactive medical questionnaire presentation device 20 embodying the invention is shown in FIG. 1, in the Question & Answer (Q&A) mode used by a patient. Preferably it is battery-powered and about the size of a book or calculator so that a patient can operate it on his or her lap, or at a desk or table. Built in to an operating panel 20a are a text display 22 and a patient keypad 26.

The operating panel also has a control keypad 36 which is kept inconspicuous or hidden from the patient. For example, the control keypad may be concealed by a translucent plastic sheet, but have labeled keys that can be illuminated to make the key labels visible from behind the translucent sheet. Or the control keypad can be hidden from the patient behind a sliding panel or the like.

Yet another alternative for the control keypad 36 is to provide a row of small, unlabeled, switch buttons 39 just below text display 22. When these switches 39, which can be membrane switches or non-moving capacitance-sensitive switches, are activated by a medical staffer, numerical labels for them (not shown) can be made to appear in the bottom row of display 22.

Presentation device 20 also has a back panel 20b, on which are arrayed an ON/OFF switch 21a, a control button 21b, a socket 21c for a battery recharger, a recharging lamp 21d, a printer jack 21e, and an audio output jack.

A side panel 38 of the presentation device has a recess 38a for receiving a read-only memory (ROM) cartridge 38b for updating a control program and questionnaire information.

A series of prestored YES/NO questions 24 for the patient appear one at a time on text display 22, to each of which the patient responds in turn by pressing an appropriate answer key on the patient keypad 26. Alternatively, the coded sounds for these questions can be stored in a speech ROM and converted from digital to analog to give an audio reading of the questions to the patient via a speaker or headphones using audio jack 21f.

Keypad 26 has only a very limited number of keys, such as four keys 28–34 for the choices YES, NO, NOT SURE (N.S.), and NEXT QUESTION. Pressing an answer key 28, 30, 32 causes the answer chosen to be echoed in the display as input echo 25. For example, in FIG. 1, the patient has pressed the NOT SURE key, causing the text "NOT SURE" to appear in the display as input echo 25.

However, the answer echoed on the display at 25 is not considered the patient's final answer until the patient presses a NEXT QUESTION key 34. Until NEXT QUESTION key 34 is pressed, the patient can change the echoed answer by pressing one of the other answer keys, then press the "NEXT QUESTION" key to adopt it as his or her final answer.

As will be seen below, a patient is instructed that if he or she has answered a question by pressing one of answer keys 28, 30, 32 and "NEXT QUESTION" key 34 and afterwards wants to change an answer to a previous question, the "Backup" key 34a (which may be one of the switches 39) should be pressed. Once the "backup" key 34a has been pressed, the previous question and answer are displayed. The patient can scroll back through the questionnaire as far as is necessary to find the answer to be changed.

It has been found that this very limited set of keys makes it easy for even the typical non-computer-literate patient to use the presentation device with little or no instruction. To the typical patient, these keys are as easy as, or easier than, those found in elevator controls, simple household appliances, etc.

Figure 2:
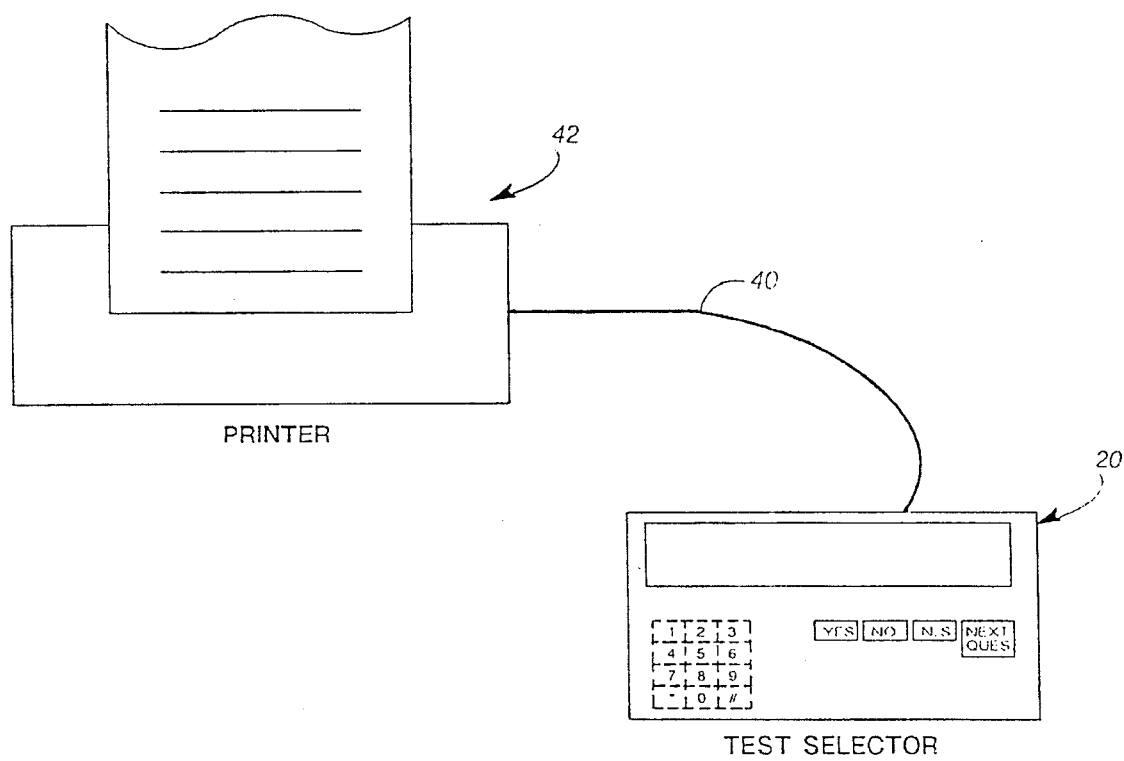
FIG. 2 is a diagram showing the questionnaire presentation device connected to a printer to produce printed output.

As shown in FIG. 2, when the patient has read and answered a full set of questions, presentation device 20 can be attached by a printer cable 40 to a standard ASCII printer 42 to print out reports based on the patient's answers. A plug (not shown) on printer cable 40 is inserted into printer jack 21e.

Preferably, the printer has an input for serial data complying with the popular interface standard RS-232C of the Electronic Industry Association, and the handshaking between the presentation device and printer is software controlled. Then cable 40 will only need three lines: a line for data and control signals transmitted by the presentation device and received by the printer, a line for data and control signals transmitted by the printer and received by the presentation device, and a ground or common connection.

In such a case, printer jack 21e and its matching plug (not shown) can be simple miniature three wire jacks, such as are found on audio equipment for connecting stereo headphones. Such jack and plug sets are compact, lightweight, and snap together and apart easily, making them much easier to use than standard 25 or 9 pin serial connectors for microcomputer equipment.

2. GENERAL METHOD OF OPERATION

Figure 3A:
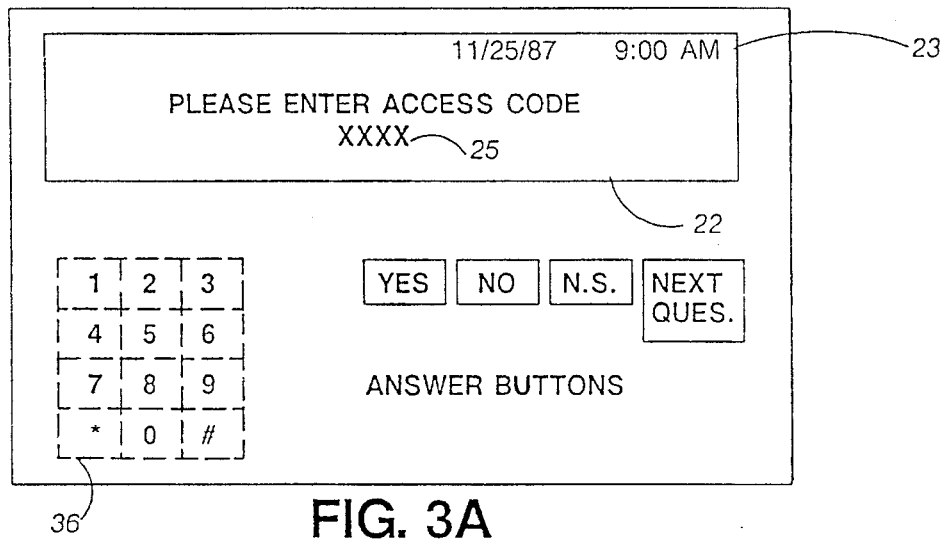

In operation, the medical staff person administering the questionnaire (hereafter "staffer") controls the mode of the presentation device by selecting from choices presented by display 22, as shown in FIGS. 3A–3F. When the presentation device is first turned on, control keypad 36 is made usable as shown in FIG. 3A, and display 22 prompts "PLEASE ENTER ACCESS CODE". In response, the staffer must enter a four digit secret access code (password) via control keypad 36. The four integers keyed in by the staffer are echoed on display 22 merely as X's to keep the access code secret.

Figure 3B:
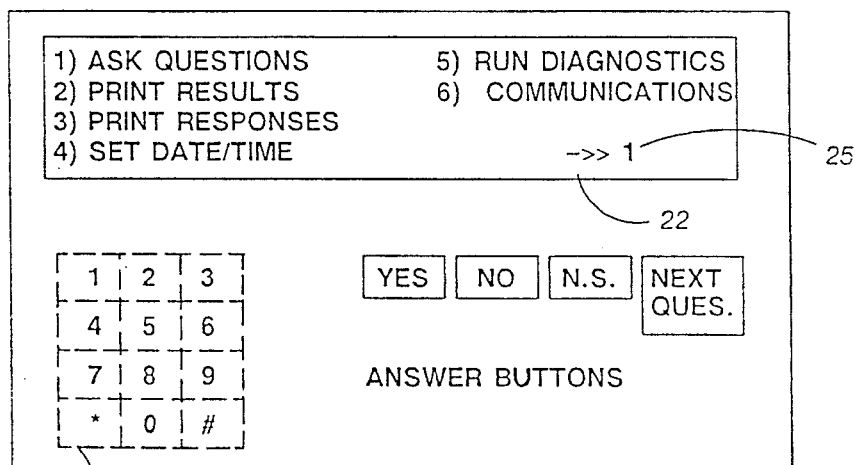

If the staffer's access code is correct, FIG. 3B, the display changes to an opening menu offering the following choices:

1) ASK QUESTIONS
2) PRINT A REPORT
3) SET DATE/TIME
4) RUN UTILITIES

Figure 3C:
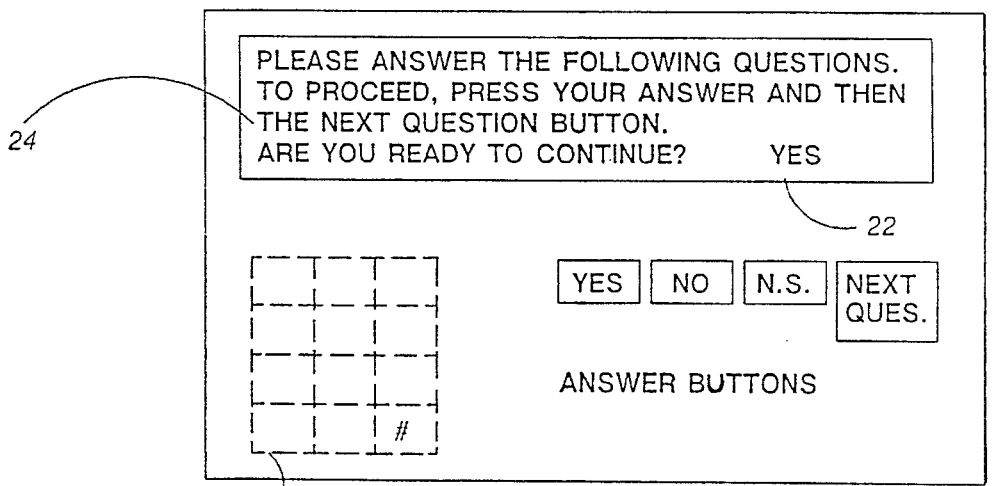

Suppose, as in FIG. 3B, that the staffer presses 1 on the control keypad for the selector to administer a questionnaire to a patient. Preferably, the staffer enters demographic data and objective information concerning the patient's medical condition which may be used in the reports printed by the device. Then as shown in FIG. 3C, the illumination of the control keypad is turned off, concealing it, and the display shows an introductory message and an initial prompt for the patient to confirm that he or she has read the message:

PLEASE ANSWER THE FOLLOWING QUESTIONS.

TO PROCEED, PRESS YOUR ANSWER AND THEN THE NEXT QUESTION BUTTON.

ARE YOU READY TO CONTINUE?

Then the display shows a brief series of introductory screens about the way the patient should operate the presentation device. This introduction advances by one screen each time the patient presses an answer key followed by the NEXT QUESTION key to indicate that he or she is ready for the next instruction.

With the introductory screens completed, the first patient question appears in display 22, as shown in FIG. 3D.

When the patient has read and responded to each of the prestored questions, a message appears in display 22 asking that the presentation device be returned to the staffer for analysis. The next time any key is pressed, the presentation device displays a prompt for the staffer to enter his or her access code. If the staffer's access code is accepted, a command menu similar to that of FIG. 3B appears from which the staffer can choose the next mode of operation.

Usually the staffer's choice will be to press control key 2 to print a report for the patient's physician (see Appendix I) or a "hard copy" of the patient's questions and answers for signature by the patient (see Appendix II). The printed copy for signature can include various notices and disclosures to the patient, and follow-up questions with blanks where the patient can fill in a response. For example, if the patient has answered "YES" he or she has allergies, a follow-up question will be printed at the top of the hard copy for completion:

WHAT ARE YOU ALLERGIC TO

3. CONNECTION TO WORK STATION

Figure 4:
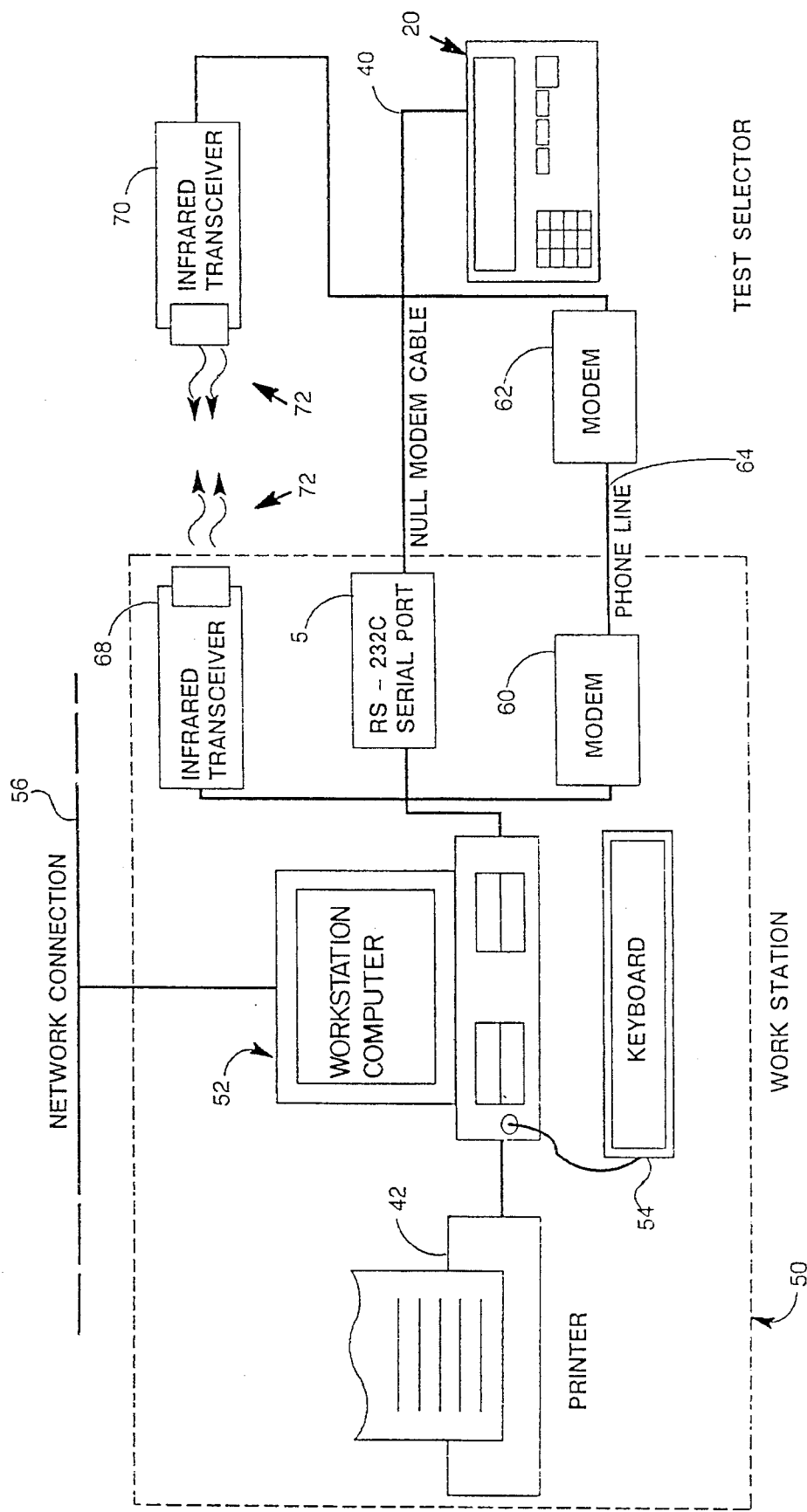
FIG. 4 is a diagram showing the questionnaire presentation device coupled to a computer terminal.

In addition to being printed out, the machine-readable reports and the patient's responses can be transmitted as shown in FIG. 4 to whatever computerized medical record-keeping or management system is being used by the patient's physician or hospital. For example, the physician or hospital may use a computerized workstation 50 having a microcomputer or terminal 52 with keyboard 54, a printer 42, and an RS-232C serial port 57 for data communications. The microcomputer or terminal 52 may be coupled to a larger system, such as a hospital or laboratory mainframe computer, by a network connection 56.

Presentation device 20 can be directly coupled by a serial cable 40 to an RS-232C interface of the workstation for exchanging data therewith. This data may include the question and answer data obtained from the patient, which may be uploaded to the workstation. Alternatively, the data may include demographic data such as the patient's name and objective data concerning the patient's condition entered by the staffer on keyboard 54 of the workstation's computer 52, which may be downloaded for use in the reports printed under direction of presentation device 20.

If the presentation device is being used in a location remote from the work station, each can be coupled for communication to a common phone line (external or intercom) by respective modems. In a preferred embodiment of the invention, an internal modem in the presentation device would allow the device to transmit patient information from any place where a telephone connection is available. In an alternative embodiment, to eliminate the need for actual mechanical coupling of electrical connectors, the workstation is provided with an infrared transceiver 68 which uses infrared signals 72 to transfer data to and from a similar infrared transceiver 70 that is coupled to presentation device 20.

4. CIRCUIT CONSTRUCTION

Figure 5:
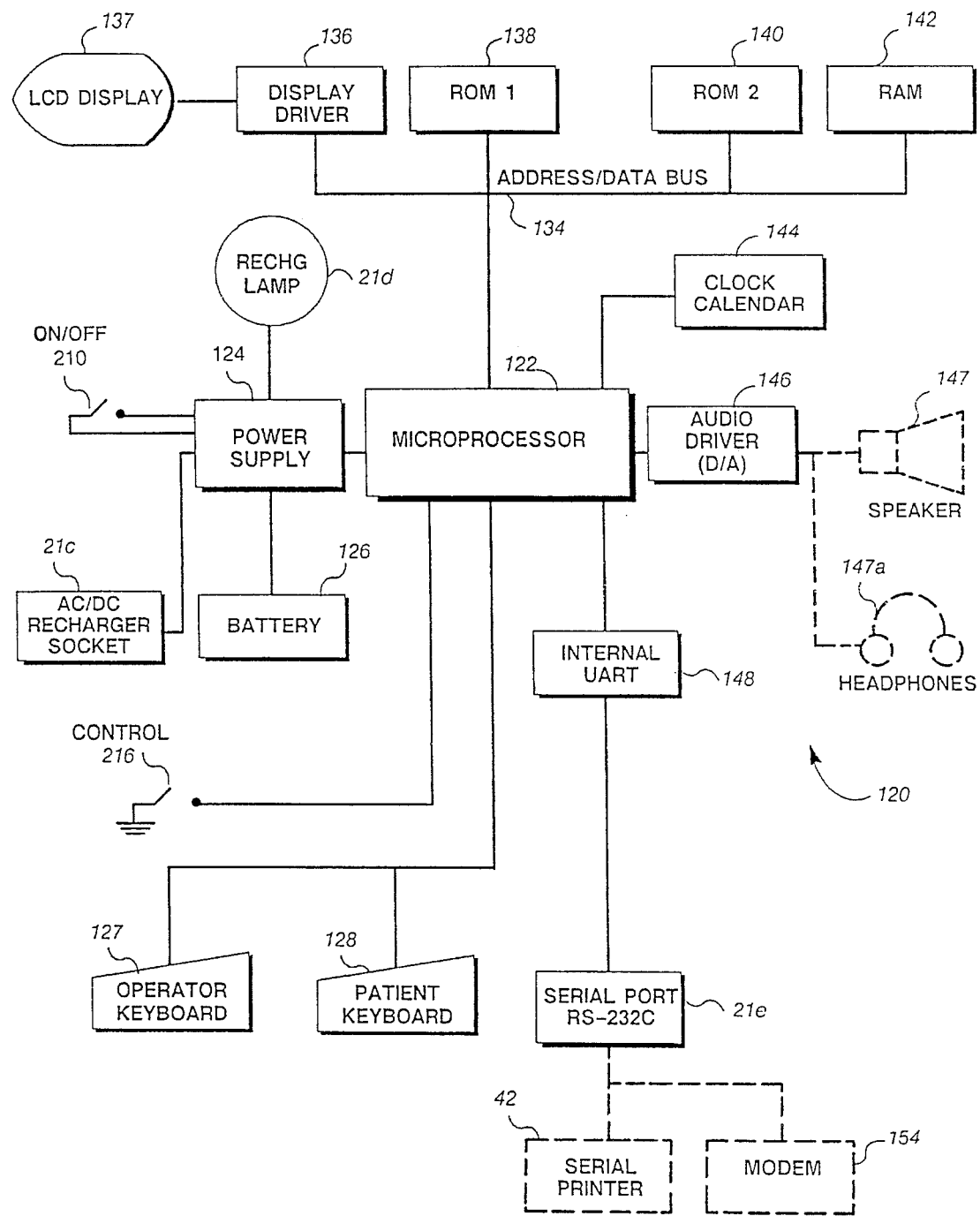
FIG. 5 is a functional block diagram of the main hardware components used in the questionnaire presentation device, and their interconnection.

The presentation device of the present invention can be conveniently and inexpensively realized by means of the microprocessor-based circuit 120 shown in the functional block diagram of FIG. 5. A microprocessor 122 receives its operating voltage from a power supply 124 that regulates the power from a rechargeable battery 126. The power supply is controlled by the ON/OFF switch 21a of FIG. 1, and can receive external electrical power for recharging battery 126 via AC/DC recharger socket 21c. Charging lamp 21d is lit whenever power supply 124 is recharging battery 126 from the external power. When battery 126 is fully charged, the charging automatically stops and charging lamp 21d goes out.

An operator keyboard 127 and a patient keyboard 128 are each coupled to ports on the microprocessor to provide digital input data from the medical staff and patients. Control switch 21b is connected to an input terminal of the microprocessor. When the patient is answering questions, the operator keyboard 127 is not illuminated to conceal it. However, if a staffer presses control switch 21b, microcomputer 122 relights control keypad 127 so the staffer can use backup key 37 of FIG. 1 to return the display to a previous question for the patient.

The microprocessor has a multiplexed address and data bus 134 by which it is able to send data bytes to a display driver 136, read-only memories ROM 1 and ROM 2, and a scratchpad random access memory RAM 142. Display driver 136 delivers ASCII text data to a display 137, which, for example, can be a supertwist liquid crystal display (LCD) capable of displaying four lines of forty characters. Preferably the character set includes not only the usual 128 ASCII characters, but an additional 128 symbols which include the international letters and symbols needed for foreign alphabets.

ROM 138 serves as a primary read-only memory in which can be stored the operating program for the microcomputer and the text used for the presentation device's questions, answers, and reports. ROM 140 is optional, and when present serves as a secondary read-only memory which stores an alternate language version of the text data for the presentation device's questions, answers, and reports. Thus, ROM 2 makes it possible for the questions, answers, and/or reports to be displayed by display 137 and/or printed out in a second language.

It is an important feature of the invention that ROMS 1 and 2 can be easily replaced by an untrained medical staffer. For example, they can be combined in ROM cartridge 38b for easy removal and insertion into recess 38a of side 38 of the test selector. This enables the control program, the questions asked, and the recommendations to the doctor to be easily updated to the latest version.

The easy interchangeability of the ROMs also facilitates use of the device by patients and medical staffers who are not fluent in the same languages. Suppose ROM 1 holds English text because the physician's office primarily uses English, but the patient primarily reads Spanish. If ROM 2 stores a Spanish version of the text of the questions, answers, and reports, by a software selection portions of ROM 2 can be addressed in place of those in ROM 1 to display the questions and answers in Spanish. The questions and answers, and follow-up questions can also be printed in Spanish. However, the staff can revert back to ROM 1 for an English version of the questions and answers and an English report of results to the physician.

In addition, because the ROMS are easily interchangeable, a large variety of specialized questionnaires may be provided to target specific health-related targeting particular health risks and medical conditions. It is believed that at least the following medical subject matter areas would be especially appropriate targets for specialized questionnaires:

Pre-operative Health and Risk;
Preventive Health;
Functional Health;
Women's Health;
Diet History;
Cholesterol Content History;
AIDS Risk;
Sexual History;
Occupational Health;
"Sick" Building History;
Pediatric History;
Neurology History;
Chest Pain History;
Low Back Pain History;
Wellness History;
Motivation History (with respect to change in lifestyle for health benefits);
Cancer Risk History; and
Fitness History (with respect to ability to exercise safely).

The exemplary reports and software provided in Appendices I, II, and III of this application demonstrate a set of question and report formats which have been chosen by the inventors for a pre-operative test selection environment. However, the software and hardware system described herein provides facilities easily adaptable to present any of the above-listed questionnaires to patients, accept answers, and produce an analytical report, merely by changing the text of the questions to be presented to the patient and by describing appropriate steps for analyzing the patient's answers.

A clock/calendar chip 144 is provided so that the time and date 23 can appear in the display (FIG. 3A) and be stamped on the printed reports and questionnaires. Moreover, since medical information and practice are constantly being updated, if desired the time and date information can be used to automatically check an expiration or date stored with the medical data in ROM 1. If the data in ROM 1 becomes older than this date, a notice can be included in the display or in the printouts, or the presentation device can be prevented from functioning until the ROM is updated.

If desired, an audio driver 146 can be coupled to an output port of microprocessor 122, to enable the microprocessor to send tones, sounds, or voice information to users via an external speaker 147 or headphones 147a via the audio jack 21f of FIG. 1.

To convert the microprocessor's parallel data into serial signals, microprocessor 122 includes an internal universal asynchronous receiver/transmitter (UART) 148 which is coupled to an output RS-232C-compatible serial connector 21e. To print reports, a standard serial printer 42 can be attached to connector 21e.

In the embodiment of the example, microprocessor 122 can be an eight-bit Hitachi Ltd. HD6303 chip of low power CMOS construction. Mode 3 of this single chip processor configures it to run as a microprocessor with a sixteen-bit (64K) address bus and an eight-bit data bus. An external crystal is used to maintain a clock frequency of about 4 MHz. The relatively large 64 kilobyte (KB) external address space easily enables external RAM 142 to be a two-KB scratchpad memory, and the external ROM 138 to be provided with about 8 KB of program code and 24 KB of text and related data for the questions, answers, and reports. Moreover, there is still plenty of room for second language ROM 140.

The program for this microprocessor was written in Microtec Assembler language, which is generally compatible with the assembler language defined by Motorola for its 6800 series of microprocessors and which produces object code suitable for execution by the Hitachi HD6303. A source code listing for an embodiment of the invention is attached to this application as Appendix III. Although the software described herein has been written for execution on the Hitachi HD6303 microprocessor, it may also be executed with relatively little modification on a variety of other compatible processors which may provide greater performance, larger addressable memory, or other advantages. Of course, the methods used herein could be duplicated to produce software for execution on any general-purpose computer.

5. SOFTWARE CONSTRUCTION a. Generally

Figure 6:
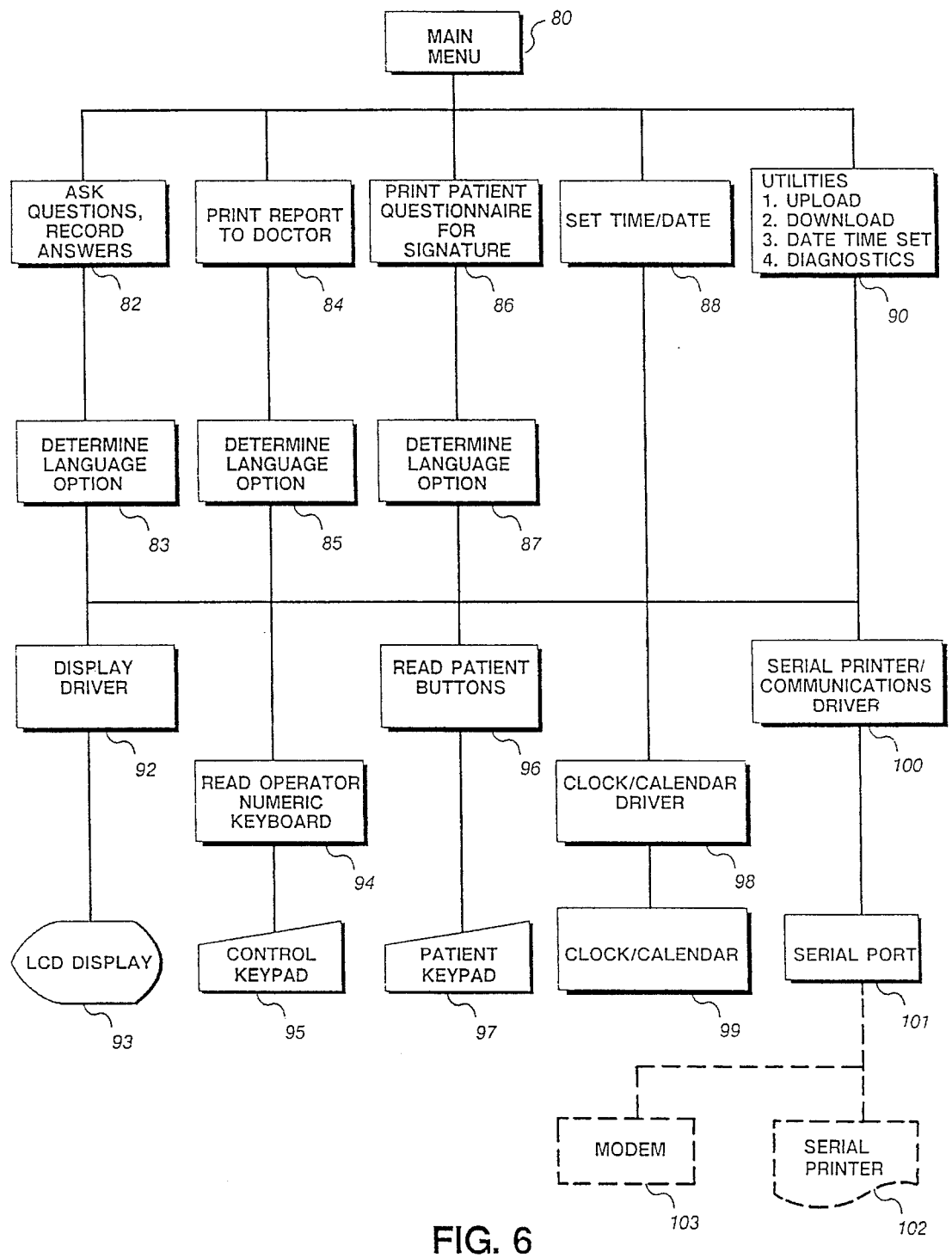
FIG. 6 is a diagrammatic representation of a program used to control the questionnaire presentation device, showing a functional representation of the systems software.

The various operations carried out by the microprocessor-based circuit of FIG. 5 are represented in the functional block diagram of FIG. 6. The main operating routine displays the Main Menu 80 (see FIG. 3B), prompting the medical staff to choose one of the main subroutines by entering a menu number via the control keypad.

The main subroutines are those for Asking Questions and Recording Answers 82, Printing a Report for the Doctor, Printing a Report for the Paitent, Printing the Patient's Questions and Answers for Signature, Setting the Time and Date 88, and various Utilities 90. If optional language ROM 2 is installed, whenever 82, 84, or 86 is selected, the language that should be used is next determined by a corresponding language option routine 83, 85 or 87.

An important feature of the invention is that reports and questionnaires can be automatically date stamped, and the medical information in ROM 1 can be automatically checked to see if it should be renewed. However, this requires that subroutine 88 be provided to enable the clock/calendar chip 144 to be properly set by the medical staff or at the factory prior to shipping.

Subroutine 90 includes various utilities, such as dedicated communication programs for uploading or downloading data to workstation 50 of FIG. 4 or running diagnostics to check circuit and data integrity.

Supporting the above-mentioned high-level subroutines are various lower-level input/output routines that interface with the hardware. Display driver 92 manages the data flow to LCD display 93. The subroutines 94 and 96 respectively get staffer and patient input from the control and patient keypads. Clock/calendar driver 98 makes clock/calendar 99 software accessible, and drivers 100 for the serial printer 102 and serial communications control input/output to serial port 101 or an external modem 103.

b. Main Menu Routine

Figure 7A:
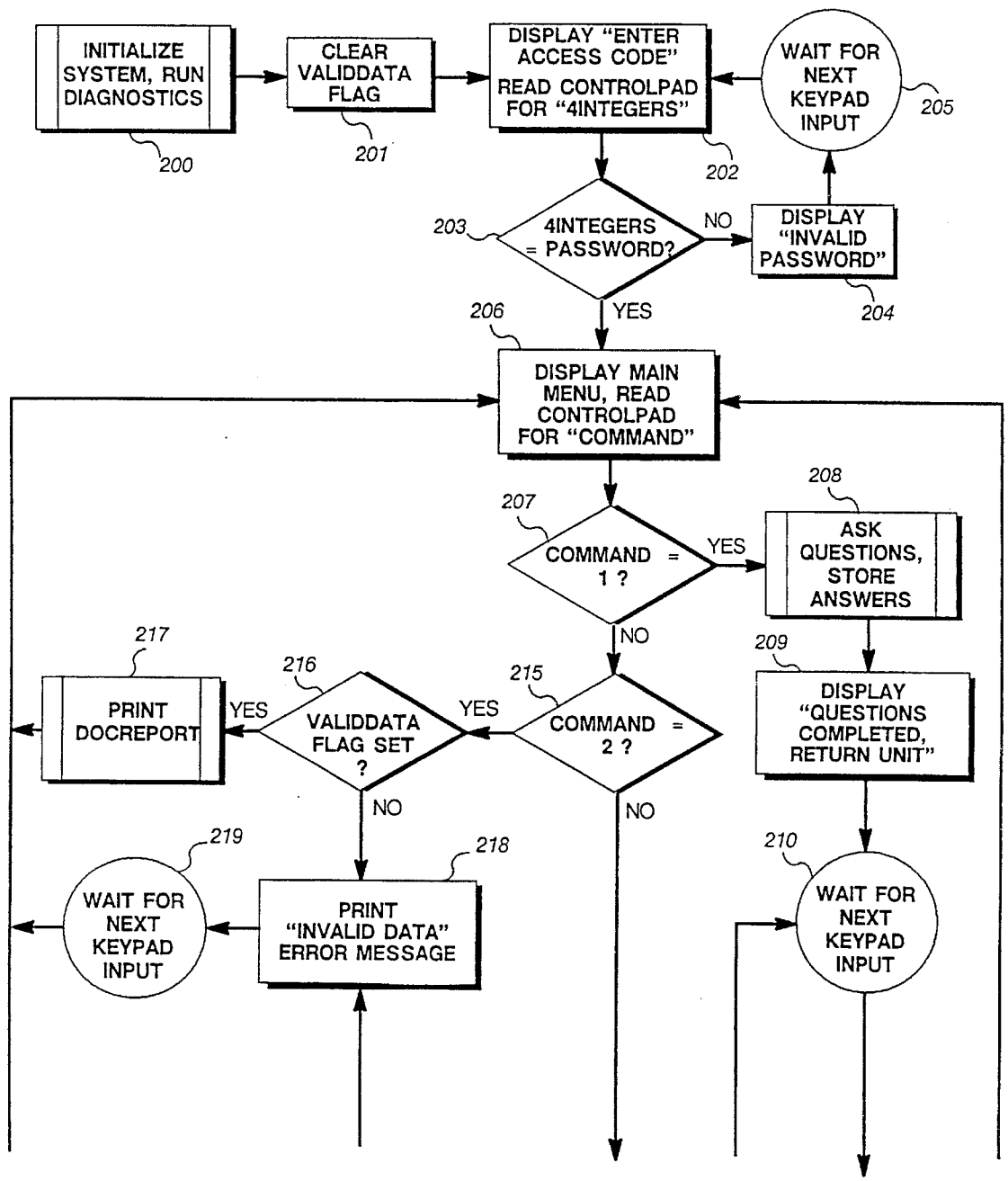
FIGS. 7A and 7B are flow-charts of the Main Menu program shown in FIG. 6.
Figure 7B:
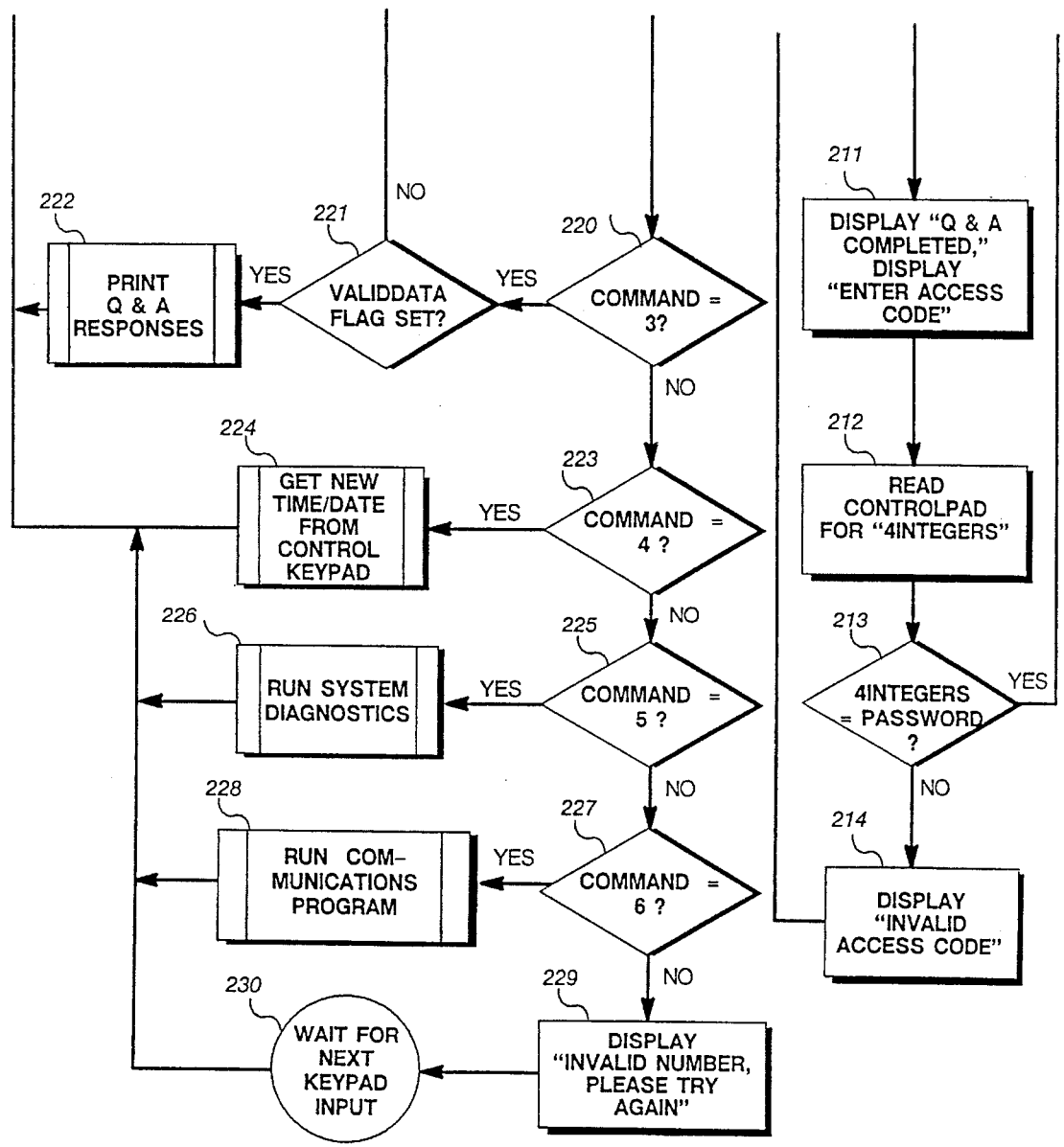

As shown in FIG. 7, Main Menu routine is the first routine called when power is provided to the microprocessor system. At Step 200 the system is initialized and diagnostics run, after which at Step 201 a flag called VALIDDATA is cleared. The message "ENTER ACCESS CODE" shown on display 22 by STEP 202, and the control pad read for the secret four-integer access code entered by the medical staffer. If Step 203 determines that the four integers read are not a valid access code, Step 204 puts "INVALID PASSWORD" on display 22, and at Step 205 this error message is left in place until there a further input is read from the control keypad at Step 202.

When Step 203 finds that a valid access code has been input, at Step 206 the Main Menu of FIG. 3B is displayed, and the medical staffer asked to enter a command integer 1–4. If the command integer is 1, Step 207 calls a subroutine ASK QUESTIONS, STORE ANSWERS at Step 208. This subroutine administers the prestored medical questionnaire to the patient and stores his or her answers. As subroutine 208 is completed, it sets the VALIDDATA flag (step not shown). Next at Step 209 "QUESTIONS COMPLETED, RETURN UNIT" is displayed to the patient. Step 210 keeps this message on the display until the next keyboard input.

When the patient returns the presentation device to the medical staffer, and a key of the control pad is touched, the wait at Step 210 ends and "Q&A COMPLETED, ENTER ACCESS CODE" is displayed to the medical staffer. When Step 213 find that the staffer again enters a valid four-integer access code, a jump is made at Step 214 back to the main menu display of Step 206. But if the code is wrong, a jump is made back to Step 210 to request the access code again.

Suppose that a set of valid question and answer data has been taken, a proper access code entered by the medical staffer at Step 212, and a jump made back to the Main Menu of Step 206. The medical staffer will probably now select a printout option,: for example "PRINT A REPORT FOR THE DOCTOR" or "PRINTS THE QUESTIONNAIRE WITH FOLLOW-UP QUESTIONS," etc.. If command integer 2 is selected, Step 207 will be a "NO" and Step 215 will be a "YES". Step 216 then checks to see if the VALIDDATA flag is set to avoid printing partial, meaningless, or corrupted data. If VALIDDATA flag is set, at Step 217 a subroutine PRINT DOCREPORT prints a report with test recommendations for the doctor. An example of such a report appears as Appendix I.

If at Step 216 the VALIDDATA flag is found not to be sent, a jump is made to Step 218, which prints an error message "INVALID DATA", after which Step 219 waits for the next keypad input and then causes a jump back to the Main Menu 206.

When the "PRINT QUESTIONNAIRE WITH PATIENT ANSWERS" option is selected by the staffer, Steps 207 and 215 are both "NO", and Step 220 is "YES". This causes Step 221 to check if the VALIDDATA is set: if it is, the PRINT Q&A RESPONSES subroutine of Step 222 prints the questions and the patient's answers, and then jumps back to the main menu. But if Step 221 finds that the VALIDDATA flag is not set, a jump is made to print the error message of Step 218, pause until the next key input at step 219, and jump back to the main menu of Step 206.

Of course, the staffer may select a housekeeping function at Step 206, such as command integer 3, which passes as a "NO" through steps 207, 215, and 220, but is a "YES" for Step 223. This causes the subroutine of Step 224 to get a new time or date from the control keypad, i.e., let the medical staffer set the clock/calendar.

Or the staffer may select command integer 4, which at Step 227 causes a communications subroutine 228 to run so that data or patient information, such as medications, birthdate, or responses to questions, can be transferred to or from the presentation device to a work station or the like.

If the command integer is other than 1–4, the program will pass to Step 229, which puts "INVALID NUMBER, PLEASE TRY AGAIN" on the display. After a wait at Step for 230 for keypad input, the routine jumps back to the Main Menu. Note that, barring a software failure within a subroutine, the Main Menu routine runs in an endless loop.

c. Accommodating A Second Language

Figure 8A:
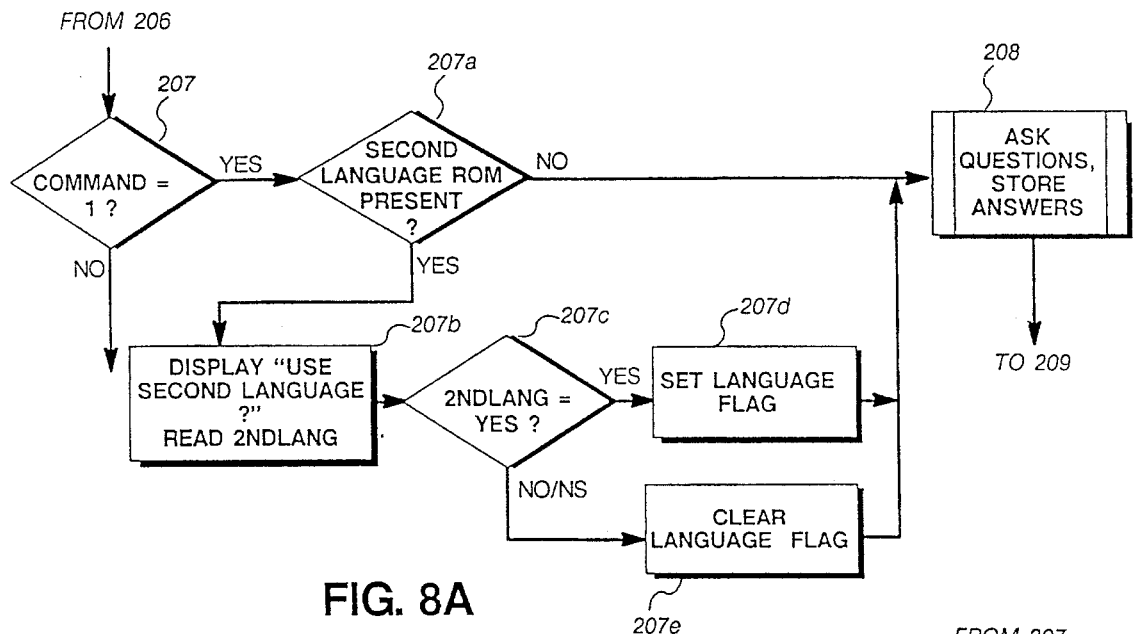
FIGS. 8A, 8B, and 8C are partial flow-charts showing how portions of the program of FIGS. 7A and 7B can be modified to give the option of a second language for the display and printed reports of the questionnaire presentation device.

If the second language ROM 2 of FIG. 5 is present, there must be additional steps added to the Main Menu routine to allow the option of using the second language. For example, the partial flow-chart of FIG. 8A adds such steps in FIG. 7 between steps 207 and 208. If in FIG. 7 command integer 1 is selected, Step 207 of FIG. 8A is "YES" transferring control to Step 207a, which checks to see if an additional language ROM 2 is present. If it isn't, Step 207a is a "NO" and the normal path to the subroutine of Step 208 is followed.

But if the second language ROM 2 is present, a "YES" at Step 207*a* causes Step 207*b* to put "USE SECOND LANGUAGE?" on display 22 The staffer's response is either "YES", "NO", or "NOT SURE" read from the Patient Keypad, which is stored as 2NDLANG. If 2NDLANG is a "YES" at Step 207*c*, a LANGUAGE flag is set at Step 207*d*, and the program moves on to subroutine 208. Subroutine 208 can then check to see if the LANGUAGE flag is set, and if it is, get text for display 22 from locations in ROM 2 rather than in ROM1, causing the second language to be displayed to the patient.

Even if the second language ROM 2 is present, the staffer may have decided to use the primary language, in which case 2NDLANG will be a "NO" or NOT SURE at Step 207*c*, and the LANGUAGE flag will be cleared at Step 207*e* before a branch to subroutine 208.

Figure 8B:
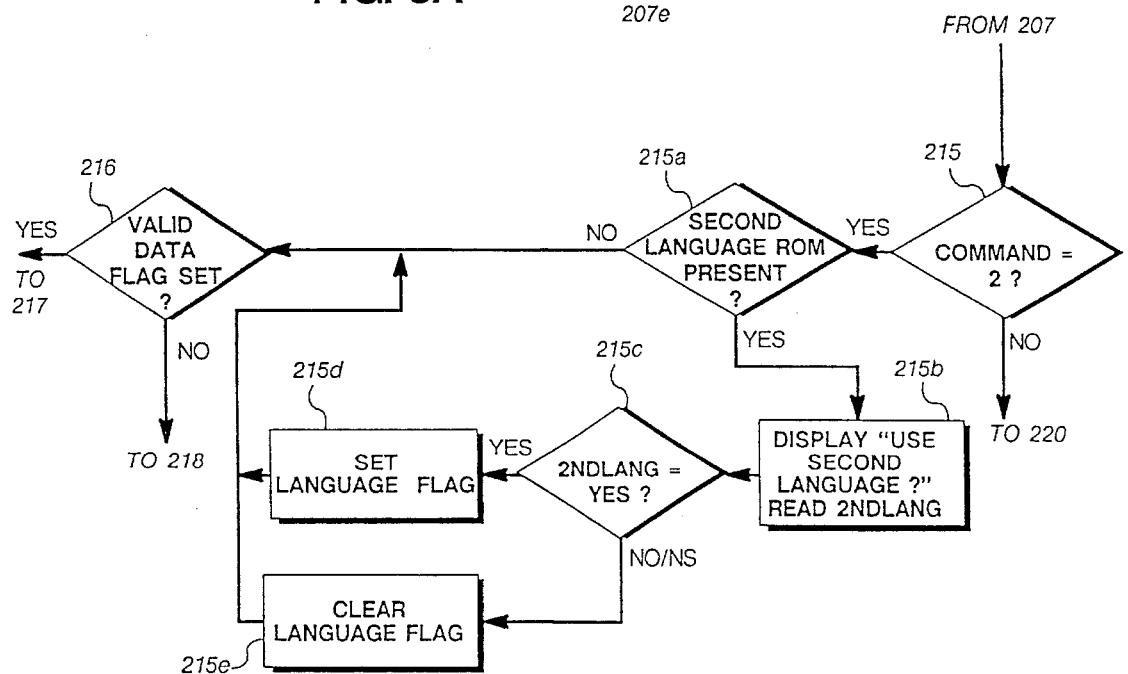
Figure 8C:
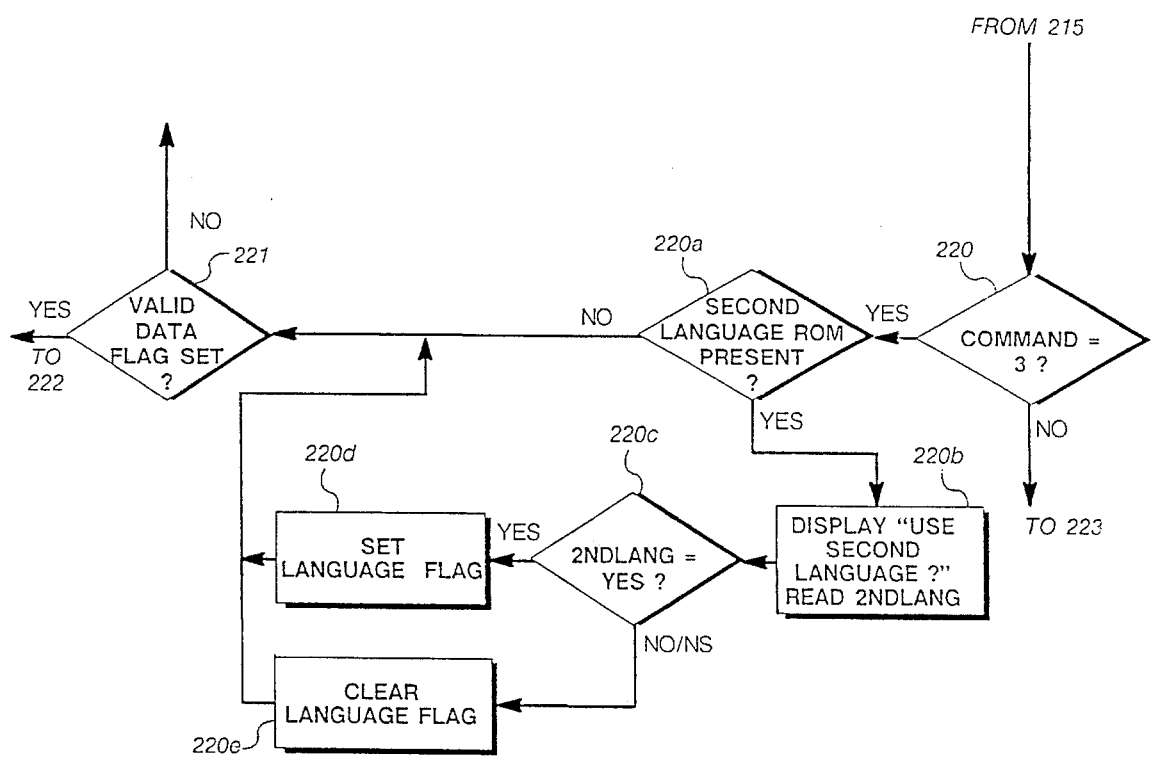

In a similar manner, as shown in FIG. 8B, second language steps can be inserted between Steps 215 and 216 of FIG. 7 to affect the language in which the Doctor's Report is printed. If Step 215*a* finds that ROM 2 is not present, the usual transfer to Step 216 to check the VALIDDATA flag is made. But if ROM 2 is present, Step 215*b* puts the question "USE SECOND LANGUAGE?" on the display. If the staffer enters "YES" on the patient keyboard, this is detected by STEP 215*c*, and the LANGUAGE flag is set at Step 215*d*. Subroutine 217 of FIG. 7 can check to see if the LANGUAGE flag is set, and if it is, get text for printing from locations in ROM 2 rather than in ROM 1, causing the second language to be used for the Doctor's Report.

If the staffer instead enters "NO" or "NOT SURE", Step 215*e* clears the LANGUAGE flag and jumps to Step 216.

The additional steps of FIG. 368C work in a manner similar to those of FIG. 8B, except that they are inserted between Steps 220 and 221 of FIG. 7 and it is the PRINT Q&A Responses subroutine 222 that must use the 2*d* language text in ROM 2 if the LANGUAGE is set.

d. Ask Questions and Store Answers

Figure 9A:
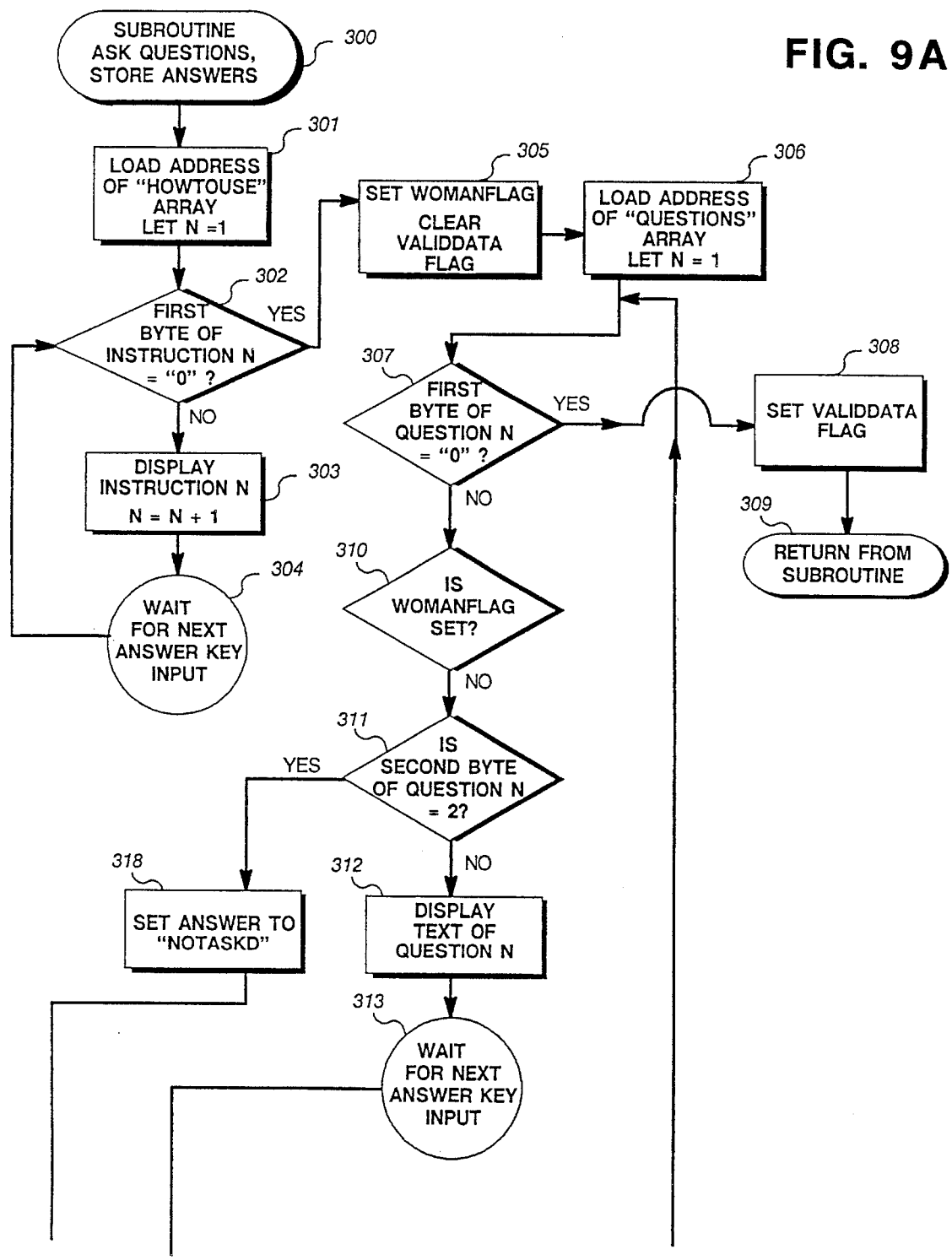
FIGS. 9A and 9B are flow-charts of a first embodiment of the "Ask Questions, Store Answers" subroutine of FIG. 7A.
Figure 9B:
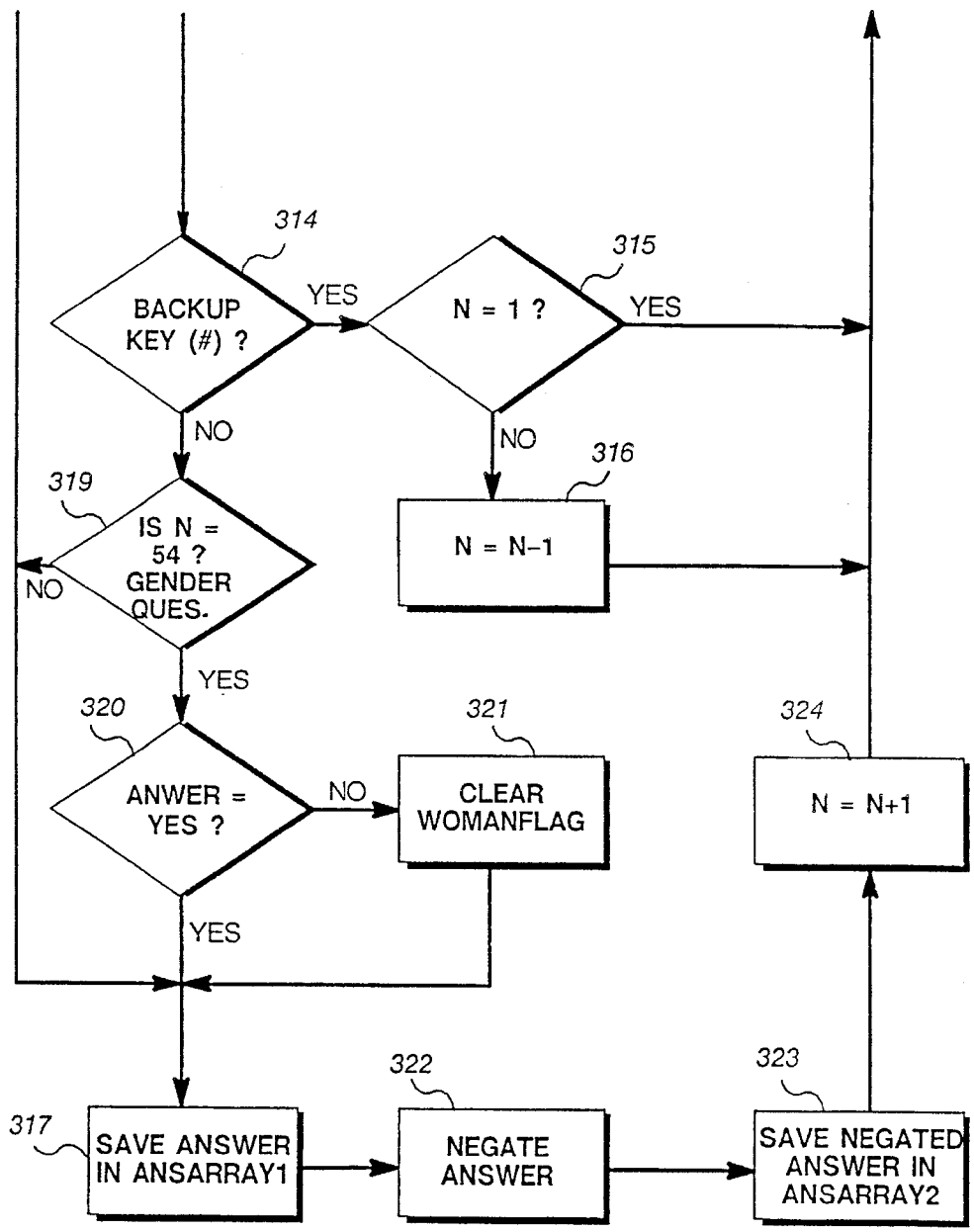

Next, FIG. 9 shows in some detail how the ASK QUESTIONS, STORE ANSWERS subroutine 208 of FIG. 7 is effected. Beginning at Step 300, the address of the array "HOWTOUSE" is loaded and saved for reference. This array has the instruction screens for the patient explaining how the presentation device keys are used to answer questions. The data for the instruction screens are saved as character strings in memory, each starting at a known location.

The last screen is a dummy which only contains one byte of data, hexadecimal 0 (0h).

Thus, Step 302 tests the first byte of Instruction N for 0h. The Instruction screens have some other hexadecimal number in the first byte, so Step 303 causes Instruction screen N to be displayed and N incremented. Then Step 304 causes a pause until the next answer keypad input, after which there is a jump to Step 302 to begin to check the first byte the next Instruction Screen.

Finally, the first byte in the last (dummy) screen is detected, indicating that all the Instruction Screens have appeared to the patient on display 22. A jump is made to Step 305 where the sex or WOMANFLAG is set as a default and the VALIDDATA flag cleared as a default.

The address of the QUESTIONS array is found and stored at Step 306, and the index N is restarted at N=1.

Before proceeding further, it is necessary to explain the format and contents related to each question stored in the read-only memory ROM 1. Each question for the patient is stored in memory as part of a Question Structure of the form:
<Question Number><Assoc Flag><Question Class><Text String>

This formatting can be understood as follows:

<Question Number> is the number of the question, except in the case of the last or dummy question, which is given a Question Number of 0h to indicate the end of the questions.

<Assoc Flag> is a code in which "0" indicates a default or ordinary question. A "1" indicates that the question has an associated text string, such as a follow-up question or a comment. A "2" indicates a question that should only be asked of females.

<Question class> is a sorting code which may be used for grouping questions according to subject matter in printed reports. For example, where the questionnaire presentation device is used in a pre-operative test application, it is desirable in printed reports to segregate the questions and instructions into the following groups:

Questions relating to laboratory tests;
Questions relating to anesthesia;
Questions relating to general health; and
User information and instructions. Accordingly, the question class code numbers could be assigned as follows:

1=Lab Test Question
2=Anesthesia Question
3=General Heath Question; and
4=User information; and the question class number would then preferably be used for sorting the questions into the appropriate groups in printed reports.

<Text String>is a string of ASCII characters making up the text of the question, including any characters reserved to represent carriage returns and line feeds, with the last byte being a 0h to indicate that the string has ended.

If <Assoc Flag> is 1, the Question Structure further includes from one to three more character strings, identified as:

<Follow-up Question String>
<YES Comment String>
<NO Comment String>

The follow-up question is necessary when the patient indicates some complication. For example, if the patient says he or she had an EKG test in the last two months, the follow-up asks where, providing a blank line to be filled in the printout of Questions and Answers.

The YES or NO comment strings put short statements in the report to the doctor of points to be noticed because of a YES or NO reply. For example, "Patient has loose teeth". "Patient may not have had an EKG in the last 2 months."

Returning to the ASK QUESTION, STORE ANSWERS subroutine of FIG. 9, at Step 307 the first byte of the Nth Question Structure in the Array is examined to see if it is 0. If it is, we must have reached the dummy question that indicates the end of the questions. A branch is made to Step 308, which sets the VALIDDATA flag and at Step 309 a Return From Subroutine is made.

However, at first N=1 and the answer at Step 307 is "NO". Although Step 310 checks to see if the WOMANFLAG is set, which initially it always is because of Step 305. Later, Question 54 will ask if the patient is a woman, clearing the WOMANFLAG if the patient answers that he is a man. Questions that follow Question 54 can then be omitted, depending on the patient's sex.

Therefore, at first the program will always jump to Step 312, which puts the text of the Nth question on the display and waits for an answer at the patient's keyboard. Assuming there is no backup to an earlier question, and the gender question (N=54) has not been reached, Step 317 saves the patient's YES, NO, or NOT SURE answer as distinguishable binary codes in the Nth entry of an answer array ANSARRAY1. At Step 322 the two's complement of the answer code is saved in a second answer array ANSARRAY2, N is incremented by Step 324 and a jump is made back to Step 307.

The reason for having a second answer array that is the negative (two's complement) of the first array is for checking against loss or corruption of data. The codes in ANSARRAY1 can be added to yield some number D. The codes in ANSARRAY2 can be added to yield some number D*, which should be the complement of D. Therefore, only if the data is not corrupted D+D*=0. That is, array ANSARRAY2 enables a simple integrity check of the data before using or printing the stored data.

Now suppose the gender question 54 "ARE YOU A FEMALE?" is reached at Step 319. The answer at both Steps 319 and 320 will be "YES" for a female, leaving the WOMANFLAG set. A male will answer "NO" at Step 320, causing Step 321 to clear the WOMANFLAG.

With the patient's sex determinable by WOMANFLAG, Step 310 becomes meaningful. As previously explained, if the second byte of a Question Structure is 2h, the question is only to be asked of females. Therefore, suppose Step 310 determines that "NO", the WOMANFLAG is not set (patient is a male), and Step 311 determines that the question's second byte indicates that it is for women only. A branch is made to Step 318, which sets the answer to "NOTASKD" (not asked). By contrast, if Step 312 does not find a 2 in the second byte of a Question Structure, the question is displayed to both males and females by Step 312.

We turn next to the backup steps 314, 315, and 316 in FIG. 9. Step 314 determines if the key pressed was the backup key on the control pad. If it was, Step 315 checks to determine if the current value of N is 1, the lowest it can be. If it is, N is not decremented, i.e. there is no backup because we are already at Question 1. But if N is greater than 1, it is decremented by Step 316, which backs up the display to the previous question. Logic for the backup mode to skip over questions that were not asked due to gender, is also built in.

As explained above, the ASK QUESTIONS, STORE ANSWERS routine ends when at Step 307 a question is encountered whose question number is 0. A branch is then made to Step 308 to set the VALIDDATA flag, after which Step 309 executes a Return From Subroutine.

e. Printing A Doctor's Report

Once a set of valid answers has been taken from the patient, from the main menu (FIG. 3B) the medical staffer can choose to print a report for the doctor. The report preferably includes the questions presented to the patient along with their recorded answers.

In addition, however, the report preferably also includes suggestions, conclusions, or inferences which may be produced through an analysis of the answers provided by the patient and objective information entered by the staffer. The software supplied in the question presentation device 20 provides several different generalized facilities for analyzing patient answers, which facilities may be useful in any of the aforementioned medical questionnaire applications.

For example, in the pre-operative test selection application which has been the subject of the exemplary embodiment described above, the report preferably includes a list of medical tests which the physician may wish to consider. Associated with each individual pre-operative test programmed into the device is a predefined rule which may indicate that that individual test should be suggested. The presentation device 20 determines which tests to suggest by examining, for each test, the predefined list of questions affecting that test and comparing the patient's answers with the answers stored in the list. A match "triggers" the suggestion of that particular test.

This method of selecting statements to be printed based on the patient's responses (or objective patient data) is not limited to medical test selection. Rather, the method can also be used to "trigger" for printing any appropriate statement, suggestion, or conclusion-including ones entirely unrelated to suggested pre-operative testing-if the printing thereof should be conditioned on the patient's responses to one or more questions. A simplified method of selecting statements to be printed is provided which is appropriate when the statement is conditioned on the patient's response to a single question.

Another method of analyzing patient answers is provided for printing a list of symptoms reported by the patient according to the anatomical system with which the symptom may be associated.

An additional method of analyzing patient answers is provided which involves calculating a weighted numerical value based on the answers. The value may indicate, for example, a numerical evaluation of the patient's general physical health, the patient's ability to function in daily life, the patient's risk from undergoing surgery, the patient's risk from undergoing anesthesia, or other appropriate values. These numerical evaluations may closely parallel certain standardized evaluations of risk, performance, or health status which are known and accepted in various medical disciplines.

In order to print the Doctor's Report, the staffer takes back presentation device 20 from the patient, and using printer port 21e of FIG. 1, connects it to a standard serial printer 42 as shown in FIG. 2. At the main menu (FIG. 3B, FIG. 7, Step 206) the staffer selects command 2. Because Step 207 is "NO" and Step 215 is "YES", next Step 216 checks to see if the VALIDDATA flag is set. If it is, there is a valid set of data to print, and subroutine PRINT DOCREPORT is called at Step 217.

Figure 10A:
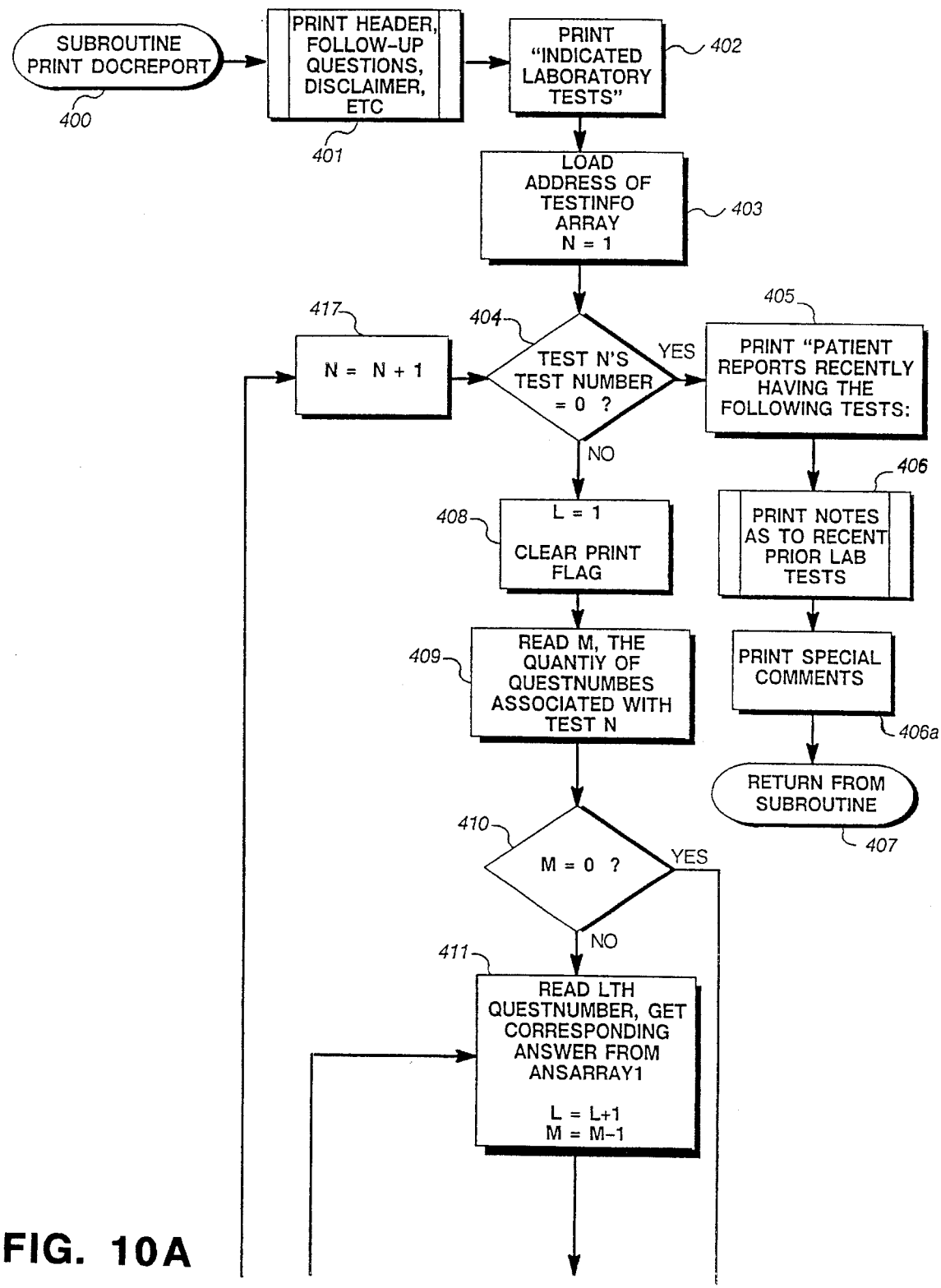
FIGS. 10A and 10B are flow-charts of the "Print Docreport" subroutine of FIG. 7A, which prints a report for a doctor.
Figure 10B:
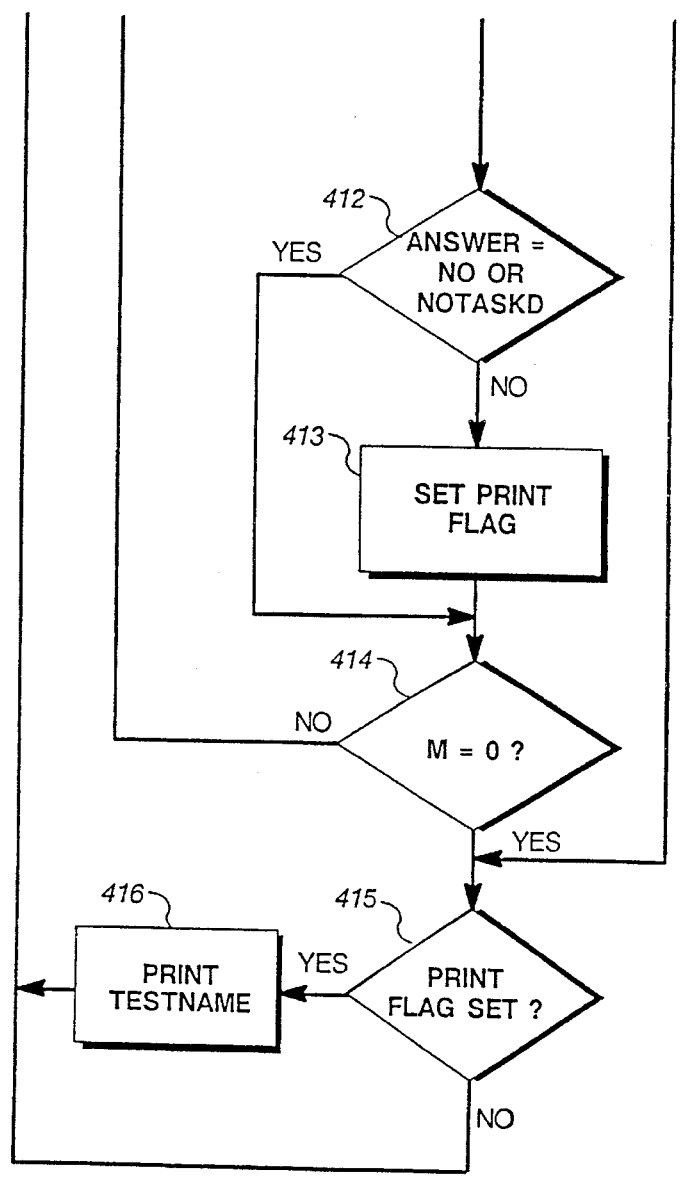

The PRINT DOCREPORT subroutine is shown in more detail in FIG. 10. The subroutine begins at Step 400 and moves to Step 401, where a header for the report is printed (see Appendix I) that includes blanks for handwritten insertion of patient information.

Next, any Follow-Up Questions associated with questions to which the patient has answered YES are printed. For example, if the patient has answered "YES", he or she has allergies, the follow-up question printed will be:

WHAT ARE YOU ALLERGIC TO?

The text of a Follow-Up Question is stored in memory in the previously mentioned Question structure after the question to which it is associated. Also stored in memory is an array called SPCQST which tells STEP 401 which YES/NO questions have associated Follow-Up Questions, which answers (YES, NO, NOT SURE) should cause a Follow-Up Question to be printed, and the address of each Follow-Up Question.

Next, Step 401 prints a disclaimer (see Appendix I) that includes information as to the basis for the test recommendations and a cutoff date beyond which the test guidelines stored in the ROM memory should not be regarded as valid because they may need updating.

As mentioned previously, the presentation device software provides several facilities for analyzing responses to questions answered by the patient and the objective data entered by the medical staffer. Each of these facilities is used to produce a portion of the doctor's report in the exemplary pre-operative test selection application described herein. However, in some questionnaire applications, it may not be necessary to use one or more of the answer analysis facilities. As will be described in greater detail, operation of each of the facilities is controlled by an array or table, so that modifying the operation of the facility may be accomplished by merely modifying the table entries, and the facility may be disabled entirely by merely providing an empty table.

A first answer analysis facility provides rule-dependent suggestions which are printed according to whether certain patient responses and objective data meet predefined criteria. This facility is used in the exemplary pre-operative test selection application to print suggestions as to laboratory tests which may be indicated by the patient's responses and objective data.

Figure 15:
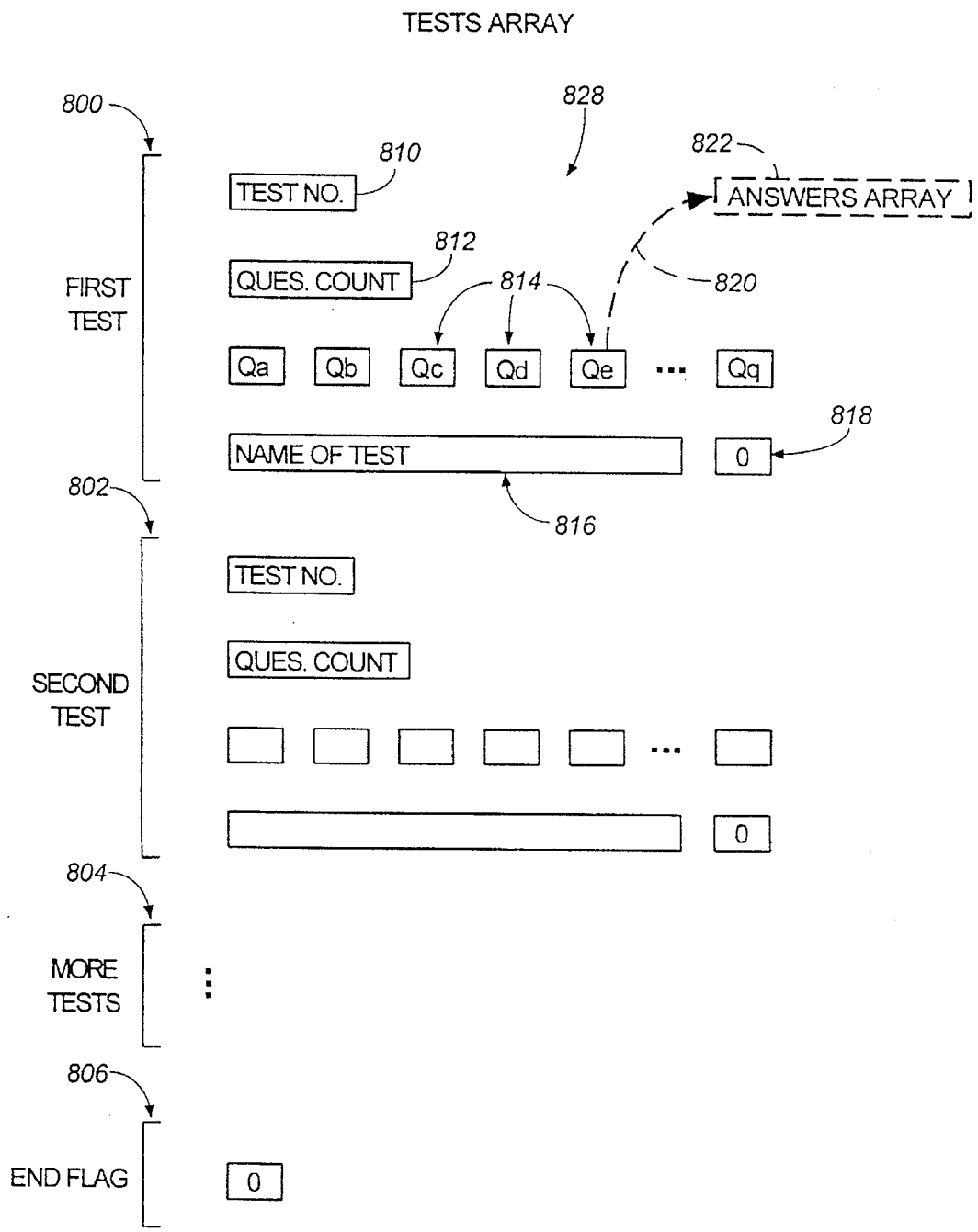
FIG. 15 is a diagram of the data structures used for storing rule-dependent suggestions used for printing recommended pre-operative tests in the "Print Docreport" subroutine of FIGS. 10A and 10B.

As best seen in FIG. 15, the rule-dependent suggestion facility is controlled by an array TESTINFO 828. For each test, there is an information entry 800, 802, 804 in the TESTINFO array 828 according to the following format:

| | |
|---|---|
| <TESTNO> 810 | The number of the test. |
| <QUESCOUNT> 812 | A number indicating how many Question Numbers are stored in <QUESADDS> |
| <QUESADDS> 814 | A series of address pointers, each indicating the address of a question that might give rise to an order for this test. |
| <TESTNAME> 816 | The name of the test (ASCII string). |

The last test entered in TESTINFO is a dummy 806, the TESTNO of which is 0 to indicate there are no more tests.

The process of printing the test suggestions portion of the doctor's report is shown in FIG. 10. Step 402 prints a heading "INDICATED LABORATORY TESTS". Then at Step 403 an indexing number N is set equal to 1, and the address of an array TESTINFO, which stores information about each test, is loaded.

Therefore, at Step 404 the TESTNO of the Nth item in TESTINFO is checked to see if it is zero. If it is, the program has reached the final or dummy test and can proceed to Step 405. However, usually the TESTNO of the Nth item in TESTINFO is not zero, and the program proceeds to Step 408, where an indexing variable L is set to 1 and a flag called PRINT is cleared.

Then at Step 409 the variable M is set equal to the QUESCOUNT associated with the Nth item in TESTINFO. If M=QUESCOUNT=0, there is no question that could give rise to an order for the Nth test, and a jump is made to Step 415. Since the PRINT flag was cleared in Step 408, the result at Step 415 will be a "NO", causing a jump to Step 417, which increments indexing variable N.

However, usually M=QUESCOUNT>0 because one or more questions could give rise to an order for the Nth test. At Step 411 the Lth question address pointer stored in the field <QUESADDS> 814 is read, and the patient's corresponding answer for this question pointed to is read from the array ANSARRAY1 822.

For example, suppose N=1, so that the printing program is computing whether to set the PRINT flag to print the name of the 1st TEST under the heading "INDICATED LABORATORY TESTS". Step 409 goes to item 1 (reference 800) of the array TESTINFO 828, where it finds the entries:

| | |
|---|---|
| <TESTNO> 810 | 1 |
| <QUESCOUNT> 812 | 13 |
| <QUESADDS> 814 | Q01, Q02, Q03, Q04, Q05, Q06, Q07, |

| | |
|---|---|
| | Q08, Q10, Q11, Q12, Q54, Q65 |
| <TESTNAME> 816 | The name of the test (ASCII string). |

Suppose the current value of L=1. Then the first (L=1) question pointer Q01 is read from the field QUESADDS 814, and used to access the information about the indicated question in the QUESTIONS array. In particular, the indicated Question Number is found to be "1" which allows the corresponding answer to be read from ANSARRAY1 822.

If at Step 412, the answer is found not to be "NO" (i.e. found to be YES or NOT SURE), Step 413 will set the PRINT flag. Later, when the program reaches Step 415, the set PRINT flag will cause the test's name 816 to be printed by Step 416.

If at Step 412 the answer is "NO", there is a jump to Step 414 so the PRINT flag will not be set. Step 414 checks to see if M=0, which would indicate that there are no more question address pointers to be read from field QUESADDS 814. If M=/0, there is a jump to Step 411 where the index variable L is incremented and the index variable M is decremented.

Thus, any of the question numbers associated with a test can, for a YES or NOT SURE answer, cause the PRINT flag to be set at Step 413. When Step 414 finds that M=0, the PRINT flag is checked by Step 415, and if it is set, the TESTNAME 816 is printed at Step 416. Then the program proceeds to Step 417 where the indexing integer N is incremented to proceed to the next test 802.

If none of the answers to the questions associated with the Nth Test has set the PRINT flag, at Step 415 the answer is "NO", and there is a jump to Step 417 where N is incremented to the next test in TESTINFO.

As mentioned above, as N is incremented, eventually the final or dummy test 806 whose TESTNUMBER is "0" is reached. Then the result of Step 404 is a YES, signalling the completion of the test suggestions phase of the doctor's report.

A second answer analysis facility provides answer-dependent statements which summarize the content of a question and the patient's response (or objective information entered by the staffer) and which are printed according to whether the patient answered YES, NO or NOT SURE to a question. This facility is used in the exemplary pre-operative test selection application to print comments regarding the patient's responses of which the physician should be aware.

Figure 16:
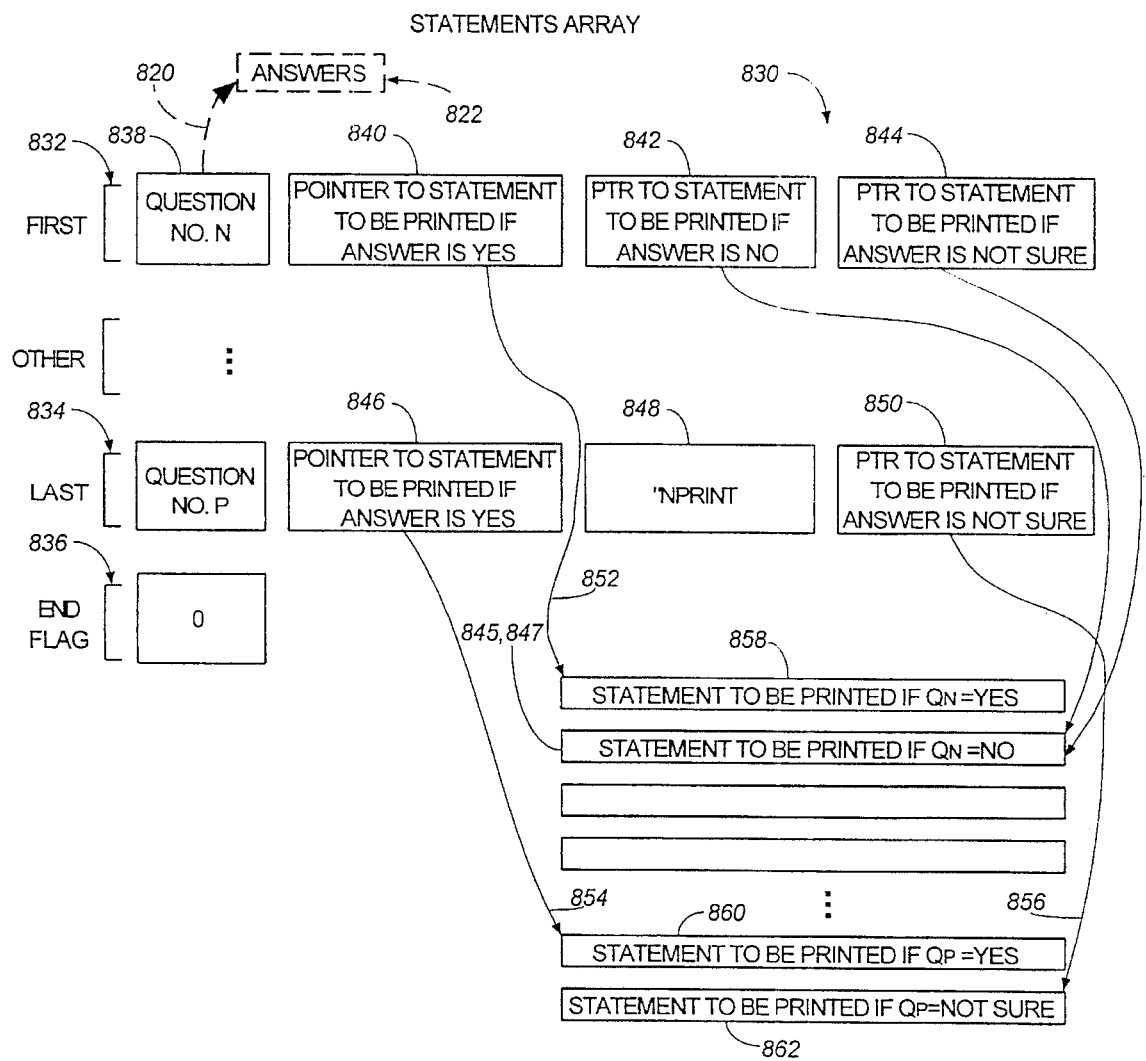
FIG. 16 is a diagram of the data structures used for storing answer-dependent statements used for printing comments regarding patient answers in the "Print Docreport" subroutine of FIGS. 10A and 10B.

As best seen in FIG. 16, the answer-dependent statements facility is controlled by the STATEMENTS array 830. For each question for which it is desired that a patient's answer trigger a comment string, a corresponding row 832 is provided in the STATEMENTS array 830. Each row consists of a question number pointer 838, a pointer 840, 846 to a statement 858, 860 to be printed if the answer to the question is YES, a pointer 842, 848 to a statement 845 to be printed if the answer to the question is NO, and a pointer 844, 850 to a statement 862 to be printed if the answer to the question is NOT SURE. If, for a particular answer, no statement is to be printed (e.g. question 834, answer NO), a special flag value "NPRINT" is stored in the corresponding pointer field 848, signalling that no statement is to be printed. If no statement need be printed for any answer to a particular question, then no entry for that question is provided in the statements array.

Returning to FIG. 10, in order to begin the test comments phase of the doctor's report, step 405 prints a heading "PATIENT REPORTS RECENTLY HAVING THE FOLLOWING TESTS:". To determine what comments should be printed about past tests, reference is then made to the array STATEMENTS 830 (FIG. 16). This array gives pointers to any YES Comment String, NO Comment String, or NOT SURE Comment String which follows a Lab Test Question. The patient's stored answers determine which of these three comment strings is printed.

For example, question 67 asks if the patient has had a blood test in the last six months. The YES Comment String 858 to be printed at Step 406 is "PATIENT HAS HAD A BLOOD TEST IN THE LAST 6 MONTHSs", and the NO and NOT SURE Comment Strings 845, 847 are "PATIENT MAY NOT HAVE HAD A BLOOD TEST IN THE LAST 6 MONTHS."

After these lab test comments are printed at the end of the doctor's report, using the above-described method and continuing processing the STATEMENTS array 830, step 406A prints Comment Strings about the patient that will be helpful to the doctor's selection of tests. For example, if the patient answered "YES" that he or she wears dentures, a YES Comment String "PATIENT WEARS DENTURES" will be printed.

A third answer analysis facility analyzes a patient's answers (or objective information entered by the staffer) and produces a weighted numerical score calculated according to a predefined algorithm. In the exemplary pre-operative test application, this facility is used at step 406b (FIG. 10) to calculate the patient's health status assessment and the patient's surgical risk assessment. In other applications, the facility could be used to generate other useful numerically expressed evaluations of the patient's responses.

Figure 17:
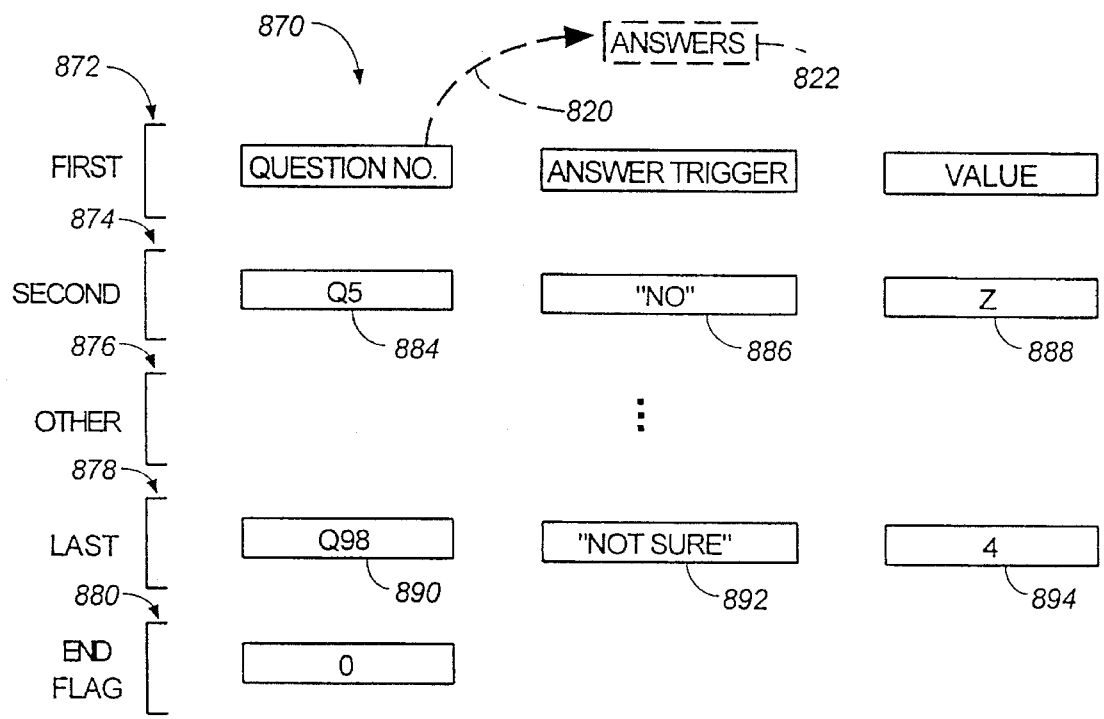
FIG. 17 is a diagram of the data structures used by the subroutines of FIGS. 10A, 10B, and 19 for calculating and printing a weighted numerical score based on the patient responses and objective data.
Figure 19:
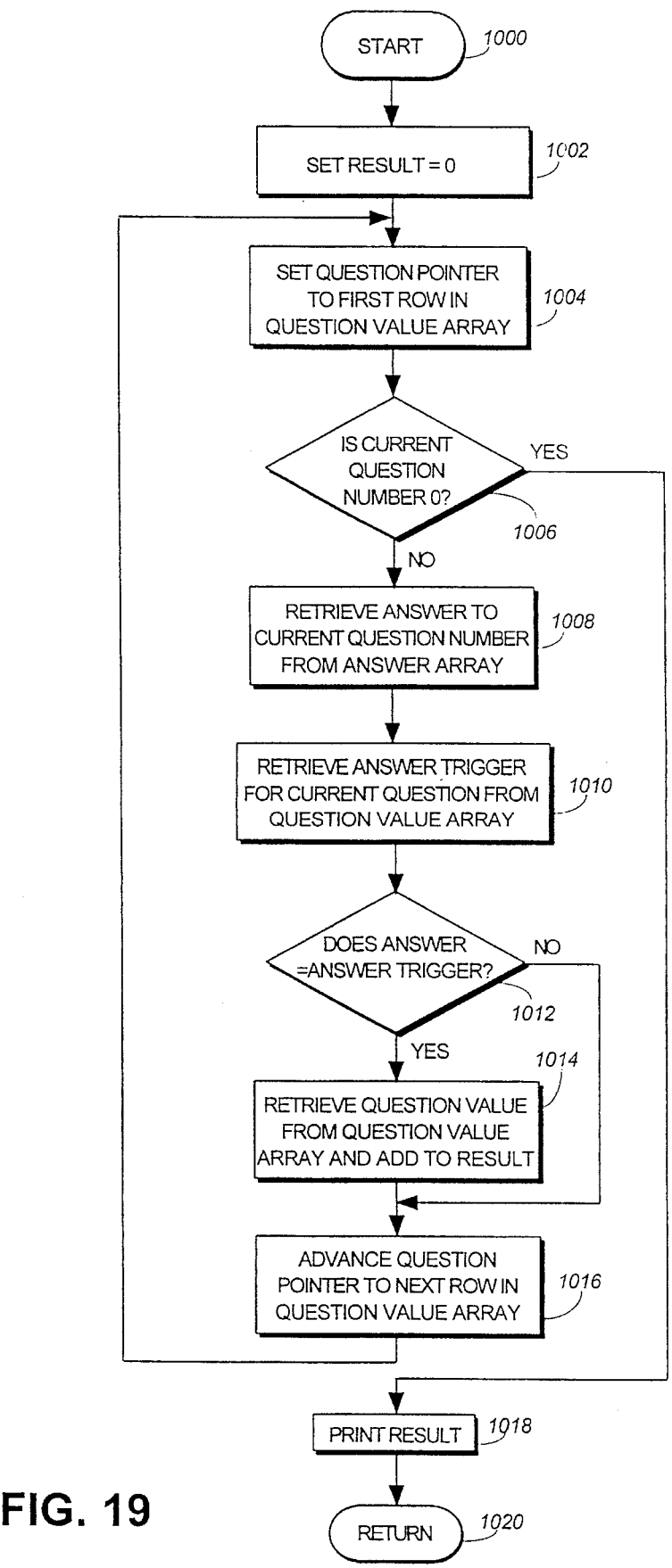
FIG. 19 is a flow-chart of a subroutine which is used by the "Print Docreport" subroutine of FIGS. 10A and 10B for calculating and printing a weighted numerical score based on the patient responses; and, FIGS. 20A and 20B are flow-charts of a subroutine which is used by the "Print Docreport" subroutine of FIGS. 10A and 10B for printing a report of patient-reported symptoms by anatomical system.

The method of calculating the numerical assessments is shown in FIG. 19. The data structure for controlling the calculation is shown in FIG. 17. For each numerical assessment to be calculated, there exists a question value array 870 which provides a list of the questions and answers affecting that assessment and the weights to be accorded each such answer. Each relevant question/answer/value triple is represented by a row 872, 874, 876, 878 in the array containing a question pointer 884, an answer prototype 886, and a question value 888 to be added to the result if the patient's answer to the question (stored in the ANSWERS array 822) matches the prototype 886. If it is desired that more than one answer to a given question affect the assessment result, additional rows having that question number may appear in the question value array with different prototype answers and question weights. For example, if is desired that either a YES or a NOT SURE answer to question 1 contribute to the assessment result, then, for each of these prototype answers, a row having question number 1 along with the answer and its associated value would appear in the array.

In the exemplary pre-operative test selection application, it is desired that the answer weights have values which may be a fraction (e.g. ¼, 1/2, 3/4, etc.). However, it is inconvenient to express fractional numbers in the question values arrays. Accordingly, each question value in the array is represented by a whole number, and the final result is appropriately scaled (in this case by ¼) before printing. In other applications, a different scale factor may be desirable.

As shown in FIG. 19, the numerical assessment subroutine begins at step 1000. In step 1002, the result storage location is cleared to zero. In step 1004, a pointer is initialized to point to the first row 872 in the question value array 870.

Steps 1006 through 1016 form a loop which is executed for each entry in the question value array 870. First, at step 1006, the question number 884 currently pointed to is checked to determine if it is zero. A question number of zero indicates that no more entries in the question value array 870 remain to be processed, and execution jumps out of the loop to step 1018. However, in most cases, the question number is not zero, indicating that the current row is an entry which should be processed. In step 1008, the patient's answer to the current question (or objective information entered by the medical staffer) is retrieved from the ANSWER1 array 822.

In step 1010, the answer prototype or trigger value 886 is retrieved from the current row of the question value array 870. In step 1012, the actual patient answer is compared with the prototype or trigger answer. If these values are not equal, then step 1014 is skipped. However if these values are equal, then at step 1014, the question value 888 from the current row of the question value array is retrieved and added to the result storage location. At step 1016, the question pointer is advanced to the next row in the question value array 870, and execution returns to the top of the loop.

The loop is repeated until all rows in the question value array 870 have been processed. Then, at step 1018, the result is scaled as required, and printed on the doctor's report. At step 1020, a return-from-subroutine is executed to return control to the calling program. If it is desired that multiple numerical assessment values be printed, a separate question values array may be provided for each such value, and the subroutine of FIG. 19 may be called to process each of these arrays.

A fourth answer analysis facility produces a report indicating cross-associations between the patient's answers (or objective information entered by the staffer) and two related subject-matter categories which may be diagnostically indicated or affected by these answers. In the exemplary preoperative test application, this facility is used at step 406c (FIG. 10) to print a list of symptoms reported by the patient organized by the anatomical systems with which the symptom may be associated. In other applications, the facility could be used to generate other reports showing an association between information provided by the patient and other diagnostic indications.

Figure 18:
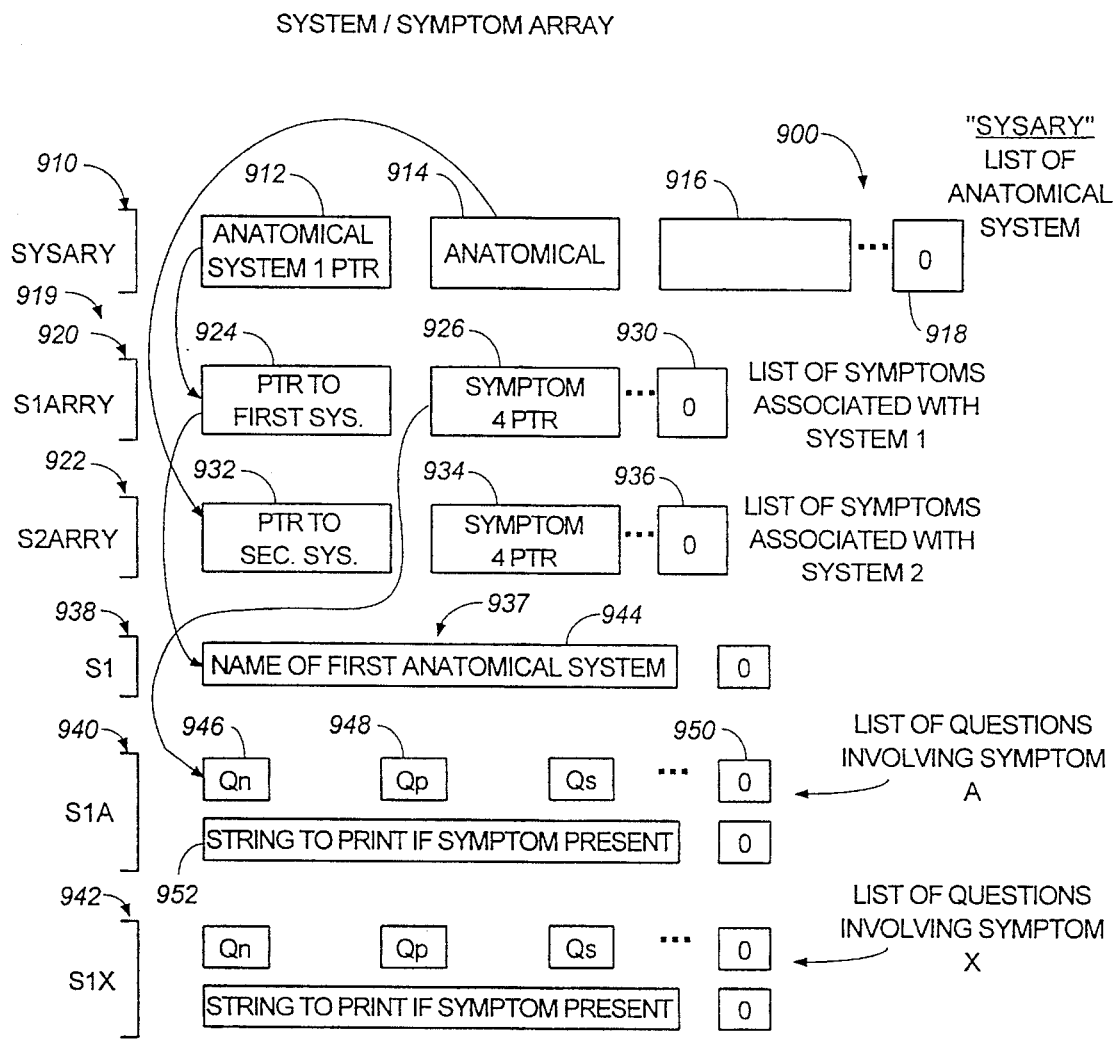
FIG. 18 is a diagram of the data structures used by the subroutines of FIGS. 10A, 10B, 20A, and 20B for printing a report of patient-reported symptoms by anatomical system.
Figure 20A:
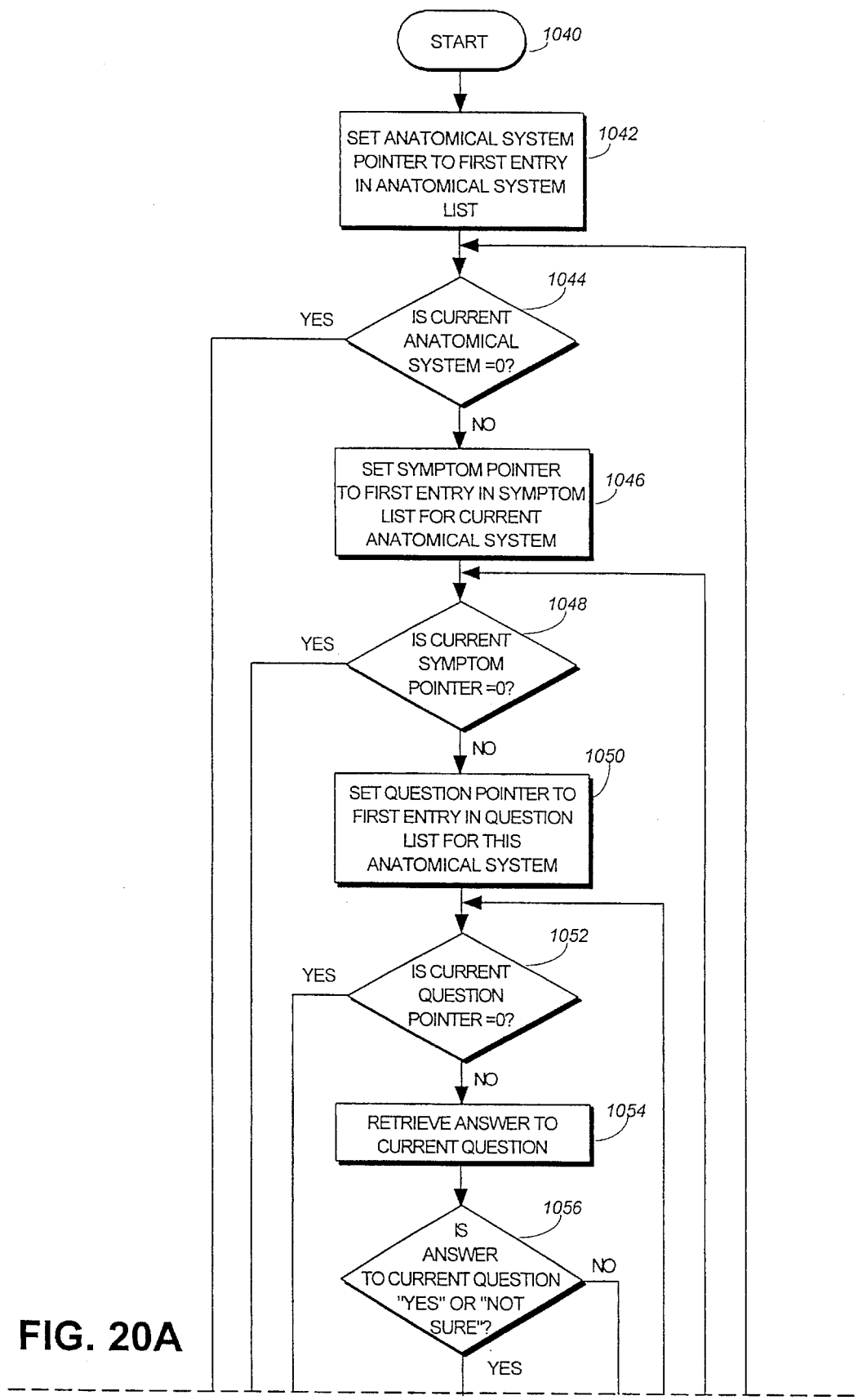
Figure 20B:
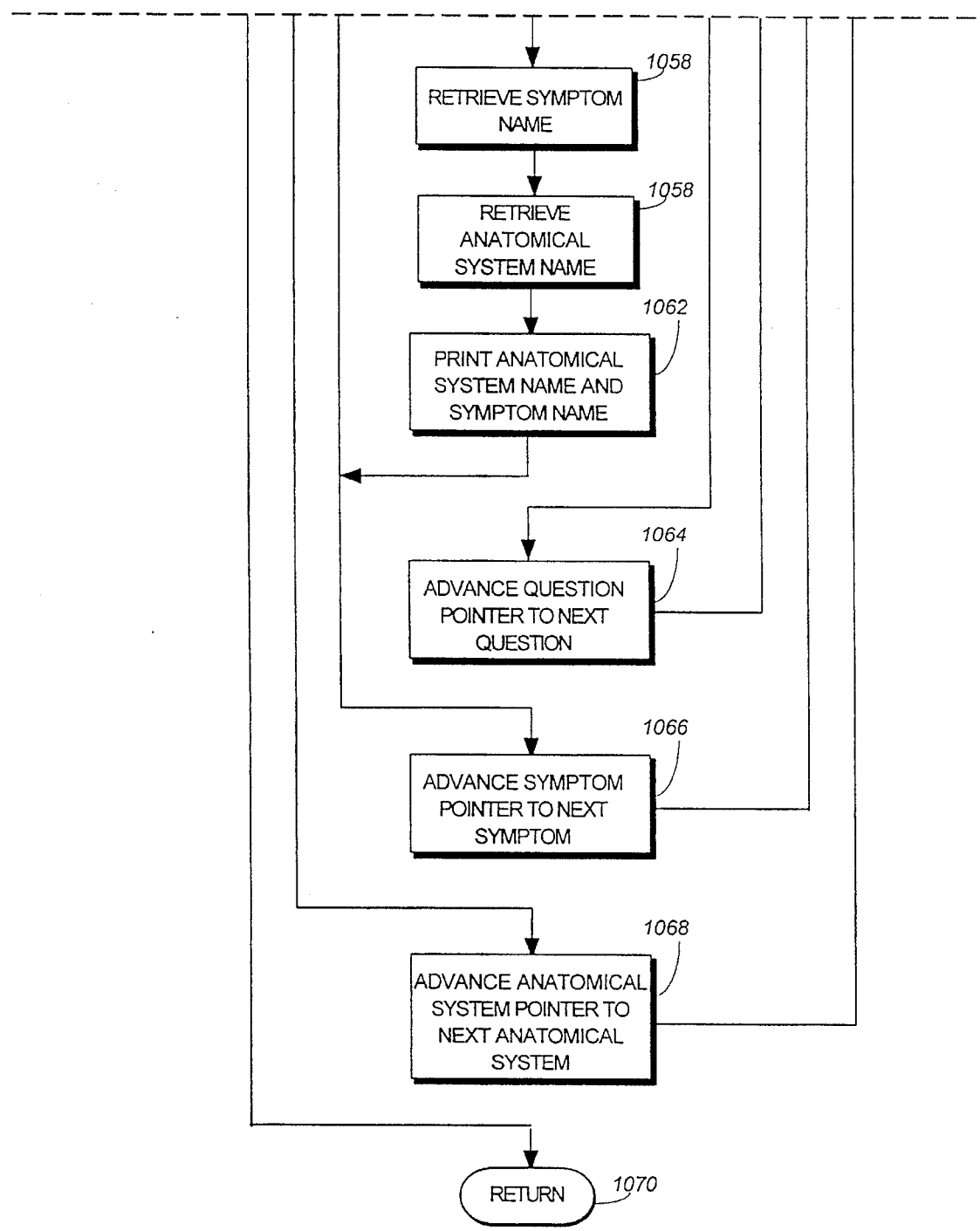

The method of producing the system-symptom report is shown in FIG. 20. The data structure 900 for controlling the method is shown in FIG. 18. The system-symptom data structure 900 comprises three related arrays 910, 919, and 937 which respectively provide increasingly greater detail concerning the represented subject matter. The primary array 910 contains a list of the available anatomical systems. The primary array 910 comprises a list of pointers 912, 914, 916 to rows 920, 922 in the secondary array 919. Each of the rows 920, 922 in the secondary array 919 represents an anatomical system and contains a list of the associated symptoms. Each of the rows in the tertiary array 937 contains either the name 944 of an anatomical subsystem (e.g. row 938), or the name 952 of a symptom associated with an anatomical subsystem and a list of questions associated with that symptom (e.g. rows 940, 942). Thus, each row in the secondary array 919 comprises a first pointer 924, 932 to a row 938 in the tertiary array 937 containing the name 944 of that anatomical subsystem, and zero or more additional pointers 926, 934 to rows 940, 942 in the tertiary array 937 representing symptoms associated with that anatomical system.

Printing of the system-symptom report begins in FIG. 20 at step 1040. In step 1042 a pointer representing the current anatomical system is initialized to point to the first entry 912 in the primary array 910.

Steps 1044 through 1068 form an outer-most loop in which each of the anatomical systems represented in the primary array 910 are processed in turn. In step 1044, the entry in primary array 910 to which the current anatomical system pointer refers is checked to determine if it equals zero. A zero is used to indicate the end of the list of anatomical systems, so that if this entry contains a zero, processing is complete, and execution jumps to step 1070. However, in most cases, the entry is not zero. Rather, it is a valid pointer into the secondary array 919, and the pointer is used to reference a row of that array. In step 1046, a second pointer representing the current symptom is initialized to the first symptom entry 926 in the current row being referenced in the secondary array 919.

Steps 1048 through 1066 form an intermediate loop in which each of the symptoms represented in the current anatomical system array entry 920, 922 (secondary array row) are processed in turn. In step 1048, the column entry in the secondary array 919 to which the current symptom pointer refers is checked to determine if it equals zero. A zero is used to indicate the end of the list of symptoms, so that if this entry contains a zero, processing of the symptoms associated with the current anatomical system (i.e. the symptoms listed in the current secondary array row) is complete, and execution jumps to step 1068. At step 1068, the anatomical system pointer is advanced so that the next system listed in the primary array may be processed, and execution jumps to step 1044.

However, in most cases, the entry is not zero. Rather, it is a valid pointer to a row 940, 942 in the tertiary array 937 containing a list of the questions associated with the symptom currently being processed. Thus, in step 1050, a third pointer representing the current question is initialized to the first question entry 946 in the current row being referenced in the tertiary array 937.

Steps 1052 through 1064 form an inner loop in which each of the questions represented in the current symptom array entry 940, 942 (tertiary array row) are processed in turn. In step 1052, the column entry in the tertiary array 937 to which the current question pointer refers is checked to determine if it equals zero. A zero is used to indicate the end of the list of questions, so that if this entry contains a zero, processing of the questions associated with the current symptom (i.e. the questions listed in the current tertiary array row) is complete, and execution jumps to step 1066. At step 1066, the symptom pointer is advanced so that the next symptom listed in the secondary array row may be processed, and execution jumps to step 1048.

However, in most cases, the entry is not zero. Rather, the entry usually contains a question pointer. The presence of a question pointer number in the tertiary array entry signifies that that question is associated with or indicates the current symptom, which, in turn, is associated with the current anatomical system. Thus, if the answer to that question is YES or NOT SURE, then the patient has reported that symptom, and the symptom and its associated anatomical system should be printed.

Accordingly, at step 1054, the patient's answer to the question (or objective information entered by the staffer) referenced by the question pointer is retrieved from the ANSWER array 822 (FIG. 15). At step 1056, the answer is checked to determine if it is YES or NOT SURE. If the comparison fails (i.e. the answer is NO), then execution jumps to step 1064, where the question pointer is advanced to the next question entry in the current tertiary array row. Execution then jumps to step 1052 for processing of any remaining questions for the current symptom. However if the comparison in step 1056 succeeds, then the current symptom and anatomical system should be printed.

At step 1058, the current symptom name 952 is retrieved from the tertiary array. At step 1060, the current anatomical system name 944 is retrieved from the tertiary array. At step 1062 the names are printed on the doctor's report. Because the current symptom and anatomical system names have already been printed, printing them again as a result of another positive question response would be redundant. Accordingly, it is not necessary to process any further questions entries for the current symptom, and execution jumps to step 1068 where the symptom pointer is advanced to the next symptom.

Once each of the symptoms associated with the current anatomical system have been processed, execution continues at step 1068, where the anatomical system pointer is advanced to the next anatomical system, and then at step 1044 where the remaining systems are processed. Once processing of all anatomical systems has been completed, execution jumps to step 1070, where a return-from-subroutine is executed to return control to the calling program.

At this point, printing of the doctor's report is complete, and at step 407, a return-from-subroutine is executed to return control to the main menu.

f. Printing Questions & Answers

If a set of valid answers has been taken from the patient, from the main menu (FIG. 3B) the medical staffer can also choose to print out the questions together with the patient's answers, including follow-up questions with blanks for handwritten answers. As in the case of the Doctor's Report, presentation device 20 is connected to a standard serial printer 42 as shown in FIG. 2 via printer port 21e.

To print the questions and answers, at the main menu (FIG. 3B, FIG. 7, Step 206) the staffer selects command 3. Because Steps 207 and 215 are "NO" and Step 220 is "YES", next Step 221 checks to see if the VALIDDATA flag is set. If it is, there is a valid set of data to print, and the subroutine PRINT Q&A RESPONSES is called at Step 222.

Figure 11:
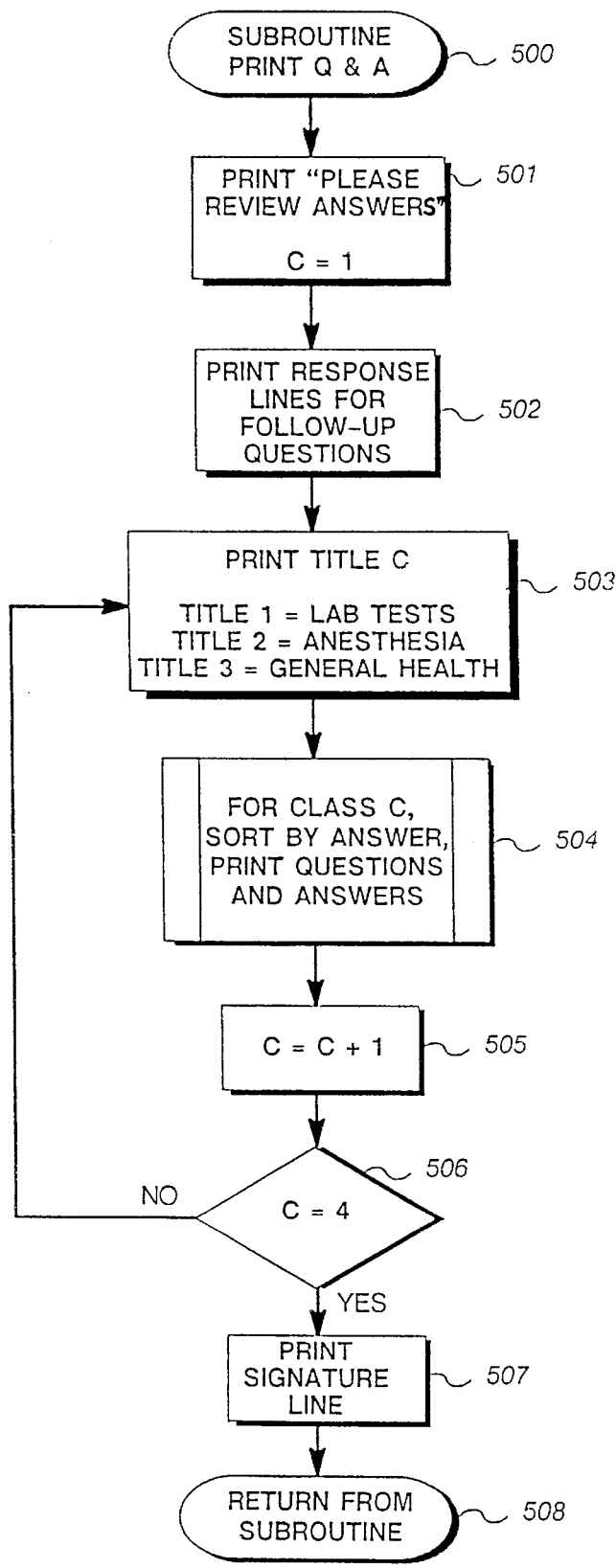
FIG. 11 is a flow-chart of the "PrintQ&A" subroutine of FIG. 7B, which prints a list of questions presented and the patient's answers, sorted by answer and question type.

The PRINT Q&A RESPONSES subroutine is shown in more detail in FIG. 11. The subroutine begins at Step 500 and moves to Step 501, where a header for the report is printed (see Appendix II). A line is printed that instructs the patient, "PLEASE REVIEW YOUR ANSWERS". An indexing variable C is set equal to 1.

Next, any Follow-Up Questions associated with questions to which the patient has answered YES are printed with blanks to be completed by the patient. This is done in a manner similar to that described for Step 401 of the subroutine PRINT DOCREPORT of FIG. 10. The Follow-Up Question is stored in memory in the Question Structure after the question to which it is associated. The array called SPCQST tells STEP 502 which YES/NO questions have associated Follow-Up Questions, which answers (YES, NO, NOT SURE) should cause a Follow-Up Question to be printed, and the address of each Follow-Up Question.

The questions are divided into groups separated by titles printed at Step 503. The title printed at Step 503 depends on the current value of the variable C: 1=LAB TESTS, 2=ANESTHESIA, 3=GENERAL HEALTH. For each value of C (1, 2, 3), Step 504 calls the subroutine SORT AND PRINT QUESTIONS AND ANSWERS of FIG. 12 to print the questions and answers having the Question Class which corresponds to the current title. Within a title, the order of printing is questions answered "YES", questions answered "NOT SURE", and questions answered "NO". For example, when C=1, calling the subroutine of FIG. 12 will only cause the questions and answers related to LAB TESTS to be sorted out and printed in this order.

Then at Step 505, the variable C is incremented so questions and answers under the next title can be printed. Assuming that there are just three titles, a check is made at Step 506 to see if C=4. If it does not, there is a jump back to Step 503 for the next title. But if C=4 at Step 507, there are no more titles and a signature line for the patient is printed under the words "THE ABOVE ANSWERS ARE CORRECT AS TYPED". After the signature line is printed, there is a Return From Subroutine at Step 508.

Figure 12:
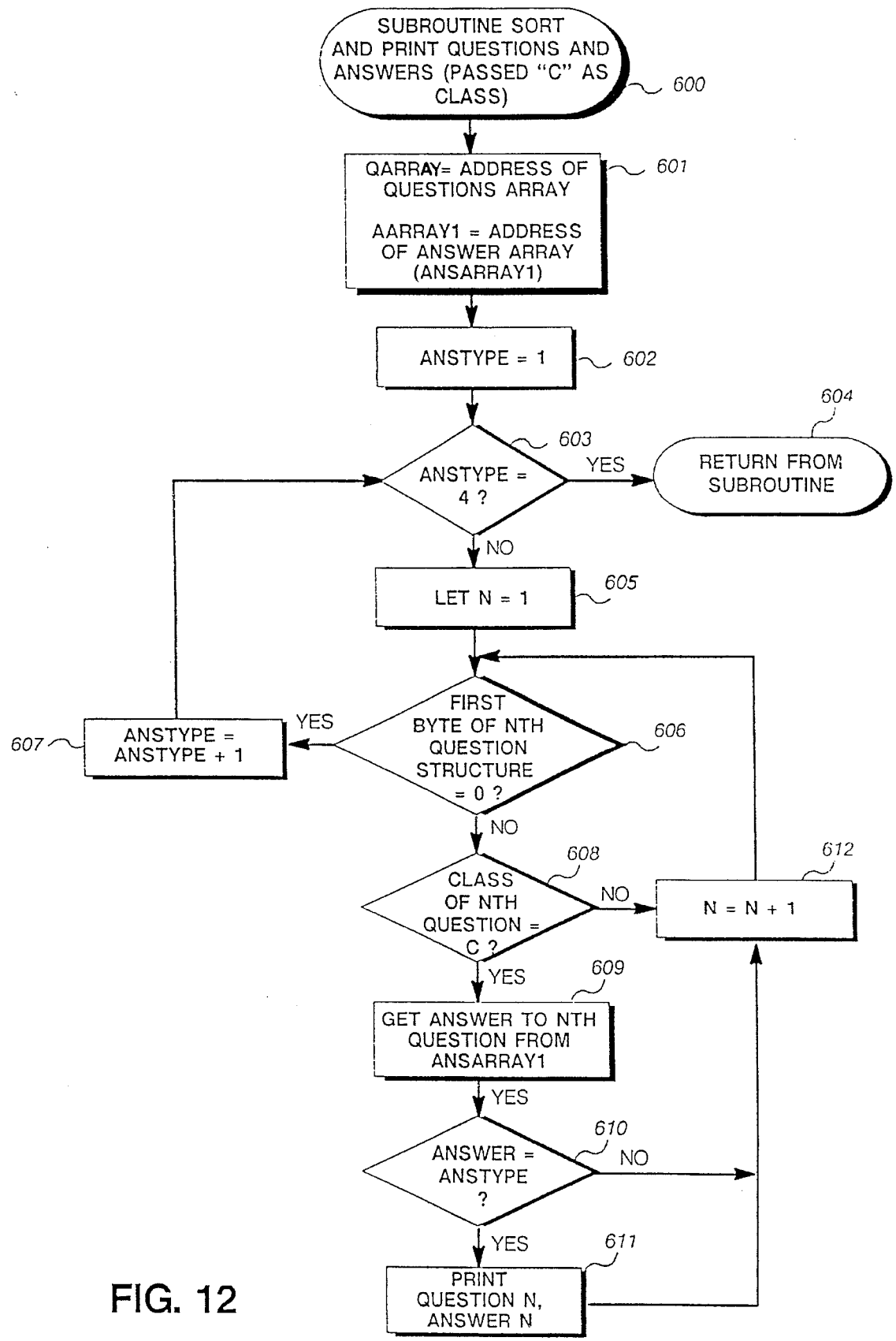
FIG. 12 is a flow-chart of the "SORT AND PRINT QUESTIONS AND ANSWERS" subroutine used in the PrintQ&A subroutine of FIG. 11.

The SORT AND PRINT QUESTIONS AND ANSWERS subroutine is shown in more detail in FIG. 12. The routine begins at Step 600 with some given value of C (1, 2, or 3) from the calling subroutine of FIG. 11. At Step 601 the respective addresses of the QUESTIONS ARRAY and first ANSWER ARRAY are noted. At Step 602 an indexing variable ANSTYPE is initially set to 1.

The variable ANSTYPE has the following meanings 1=YES answer, 2=NOT SURE answer, 3=NO answer, 4=NOTASKD (end of printed answers). Therefore, at Step 603 a check is made to see if the indexing variable ANSTYPE equals four. If it does, there is a Return From Subroutine at Step 604.

However, initially ANSTYPE is one because of Step 602, and the program proceeds to Step 605 where an indexing integer N is set to 1. Then at Step 606, the first byte of the Nth Question Structure stored in the questions array QARRAY is read. If it equals zero, the dummy Question Structure has been reached that indicates there are no more questions to process.

However, usually the first byte is not zero, in which case Step 608 compares the Question Class of the Nth Question Structure with the value of C input to the subroutine. If the Question Class does not match C, a jump is made to Step 612, where N is incremented and a jump made back to Step 606 to check the first byte of the next Question Structure.

When the Question Class of the Nth Question Structure matches the value of C at Step 608, the corresponding answer is obtained from answer array ANSARRAY1 by Step 609. If the answer matches the current value of ANSTYPE, the Question and its corresponding Answer are printed at Step 611. Otherwise, the Question and Answer are skipped by jumping to Step 612, where the variable N is incremented. Then there is a return to Step 606 to read the first byte of the next question structure.

For each value of ANSTYPE, eventually N is incremented at Step 612 until the dummy Question Structure is reached, causing a "YES" at Step 606. Then Step 607 increments ANSTYPE to the next type of answer. Eventually, Step 607 causes ANSTYPE to equal four, which is detected by Step 603 to cause a Return From Subroutine at Step 604 as mentioned above.

Thus, for a given category of question C, the subroutine of FIG. 12 first prints all the questions answered "YES", then all those answered "NOT SURE", and then all those answered "NO". Within a category, the answer given to a question determines its order in the printout.

In the first embodiment of the invention so far described, the subroutine ASK QUESTIONS, STORE ANSWERS of FIG. 9 processes each question in sequence (FIG. 13C), but if the WOMANFLAG is CLEAR certain questions only for females are not displayed (FIG. 9, Step 311) and automatically answered "NOTASKD" (not asked) by Step 318. As shown in FIG. 13A, the flag check FCh causes question Qi to be skipped when the WOMANFLAG is CLEAR and instead processing proceeds to question Qi+1.

For a male patient, if the program has to be backed up from question Qi+1, logic is built in so that backup key 37 skips question Qi and returns to previous question Qi−1, here assumed to be a general question for both men and women. Thus, this simple automatic skipping of certain questions irrelevant to the particular patient does not greatly complicate use of backup key 37.

In the subroutine PRINT DOCREPORT, which prints a report to the doctor, questions whose answer is "NO" or "NOTASKD" do not cause the associated test to be printed (Step 412). The subroutine SORT AND PRINT QUESTIONS AND ANSWERS of FIG. 12 treats questions having the answer "NOTASKD" as a forth type whose printing is skipped by the action of Step 603.

A second embodiment of the invention allows for more general branching to further questions in accordance with the patient's answers and provides a means for storing the return path needed to support backup key 37.

As shown in FIG. 13D, in the second embodiment the next step of the control program after displaying question Qi depends on whether the answer to question Qi is YES (Y) or NO (N). In the general case, as shown in FIG. 13B, we must also allow for the alternative paths to converge at certain questions, such as Q13 and Q18. To move backwards to previous questions along the correct alternative paths requires special support for backup key 37.

As shown even more generally in FIG. 13E, each question Qi can be followed by a branch to one of three different paths Y, N, NS, corresponding to YES, NO, and NOT SURE. FIG. 13F shows the tree-like structure of the possible paths of the program when the next question to be asked depends on whether the answer is YES, NO, or NOT SURE.

To enable such branching, the previously mentioned Question structure stored for each question in the QUESTIONS array is augmented as follows:

<Question Number><Assoc Flag><Question Class>
<Text String>
<Branchflag><Next/Yes Question Pointer>
[<No Question Pointer>]

The additional parts of the Question Structure which enable branching are a BRANCHFLAG, a NEXT/YES QUESTION POINTER and a NO QUESTION POINTER. If a particular question does not need branching, such as question Qi of FIG. 13C, the BRANCHFLAG is CLEAR, the NEXT/YES QUESTION POINTER is used as a pointer to the next question Qi+1, and the NO QUESTION POINTER is not present.

A question leading to a YES or NO alternative (see FIG. 13D) has its BRANCHFLAG SET. The NEXT/YES QUESTION POINTER points to the next question that should follow a "YES", and the No Pointer points to the next question that should follow a "NO". For purposes of branching, the presentation device can be designed to always treat an answer of "NOT SURE" as either a "YES" or a "NO". Alternatively, the presentation device's Question Structure can be further augmented to add a separate pointer [<Not Sure>] for a third alternative as shown in FIG. 13E.

Figure 14A:
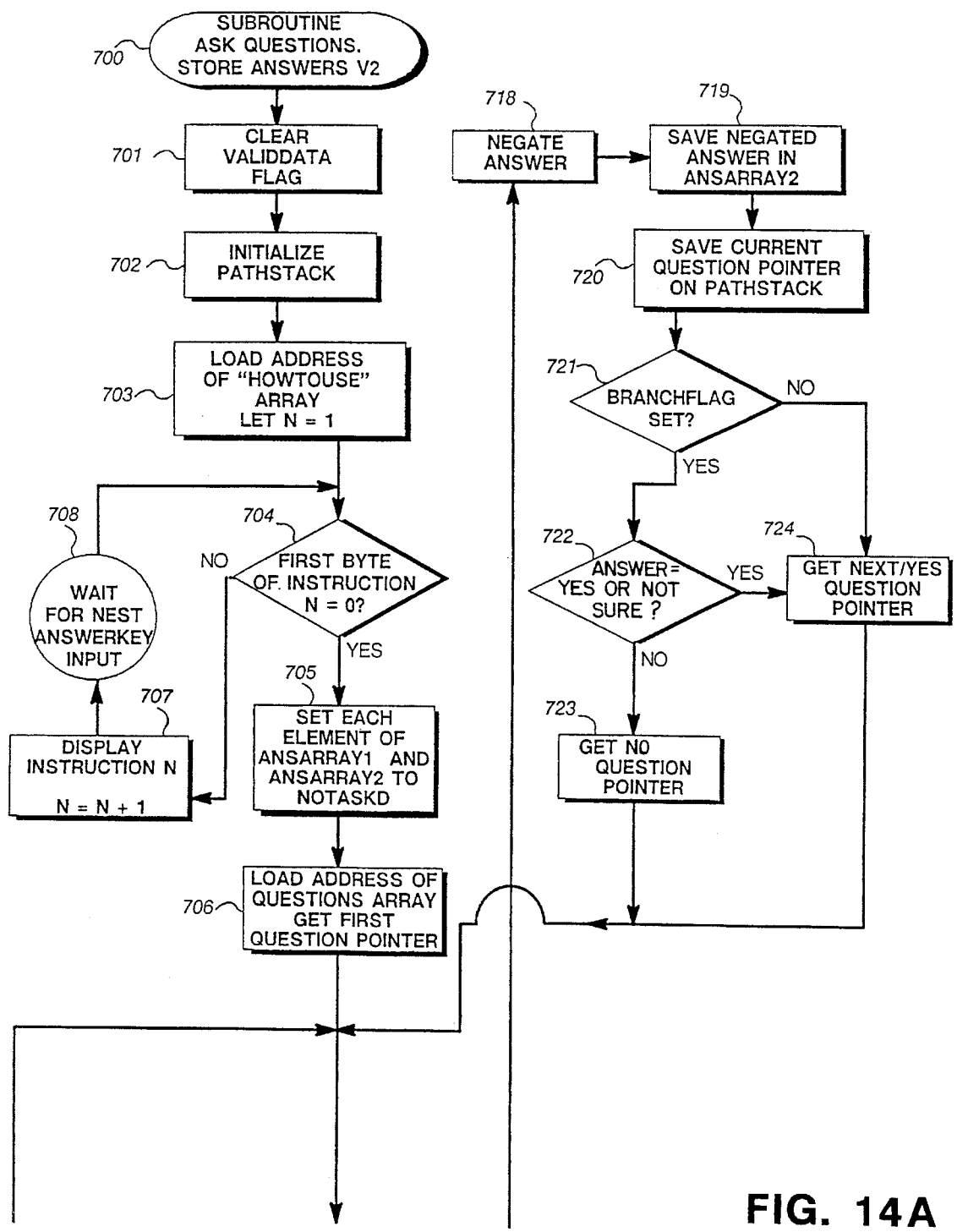
FIGS. 14A and 14B are flow-charts of a second embodiment of the "Ask Questions, Store Answers" subroutine of FIG. 7A.
Figure 14B:
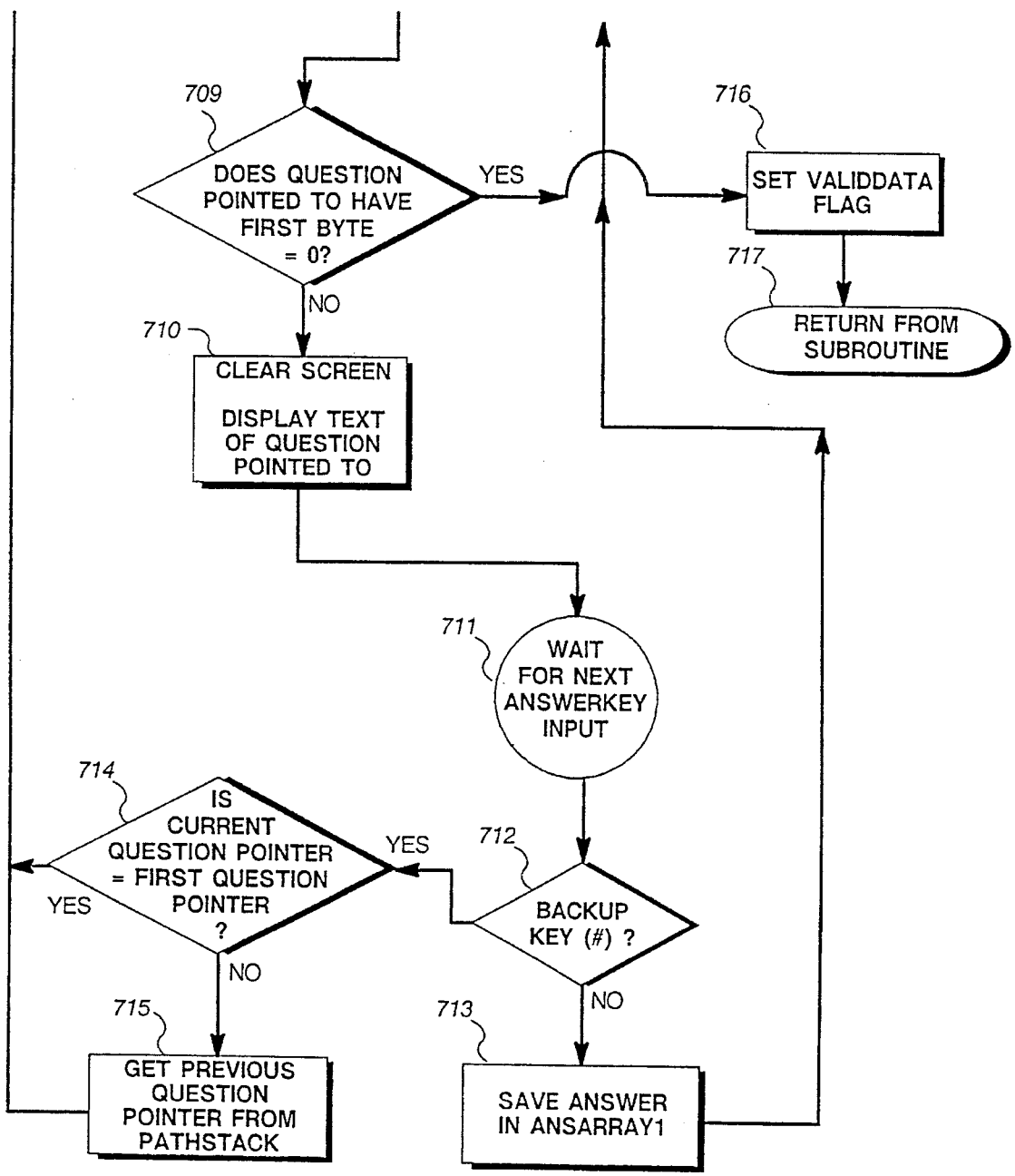

For example, to enable branching which treats an answer of "NOT SURE" like a "YES", FIG. 14 shows a subroutine ASK QUESTIONS, STORE ANSWERS V2 to be substituted for the first embodiment's ASK QUESTIONS, STORE ANSWERS subroutine of FIG. 9. Beginning at Step 700, the VALIDDATA flag is cleared at Step 701 and a portion of RAM memory 142 (FIG. 5) is initialized as a first-in-last-out stack called PATHSTACK for question address pointers. Then the address of the array "HOWTOUSE" is loaded at Step 703, and an index integer N set initially to 1.

Step 704 tests the first byte of Instruction N for 0h. Since the Instruction screens have some other hexadecimal number in the first byte, a jump is made to Step 707, which causes Instruction screen N to be displayed and N incremented. Then Step 708 causes a pause until the next answer keypad input, after which there is a jump to Step 704 to check the first byte of the next Instruction Screen. Finally, a first byte of 0h in the last (dummy) screen is detected, indicating that all the Instruction Screens have appeared to the patient on display 22. The program proceeds to Step 705 where each element of the two answer arrays ANSARRAY1 and ANSARRAY2 is initialized to "NOTASKD" (not asked).

The address of the QUESTIONS array is loaded at Step 706, and the first question pointer used to obtain the address of the Question Structure for the first question. The first byte of this Question Structure is examined at Step 709 to see if it is 0. Usually it is not, so the program proceeds to Step 710 which clears the screen and displays the text of the question pointed to. Then Step 711 waits for an answer to be input at the patient's keyboard.

Assuming at Step 712 that the backup key # has not been pressed, Step 713 saves the patient's YES, NO, or NOT SURE answer as distinguishable binary codes in an corresponding entry of an answer array ANSARRAY1. Then Step 718 determines the two's complement of the answer code, and Step 719 saves this in a second answer array, ANSARRAY2.

If instead Step 712 finds that the backup key on the control pad was pressed, Step 714 determines if the current question pointer is that pointing to the first question. If it is, there is no backup because we are already at Question 1. But if Step 714 determines that the question currently pointed to is greater than 1, Step 715 pops the pointer for the previously asked question off the PATHSTACK. Then a jump is made back to Step 709 to process the previously asked question.

After Step 719 has saved the two's complement of an answer in ANSARRAY2, Step 720 pushes the current question pointer onto the PATHSTACK. If Step 721 finds that the BRANCHFLAG is SET, Step 722 determines if the patient's answer is NO. If it is, Step 723 uses the NO QUESTION POINTER of the current question for the address of the next question to be asked, and a branch is made back to Step 709.

If instead the patient's answer is "YES" or "NOT SURE", Step 724 uses the NEXT/YES QUESTION POINTER of the current question for the address of the next question, followed by a branch back to Step 709.

If Step 721 finds that the BRANCHFLAG is CLEAR, the answer to the current question does not cause branching into alternate paths. Step 724 uses the NEXT/YES QUESTION POINTER of the current question for the address of the next question to be asked, and there is a branch back to Step 709.

The ASK QUESTIONS, STORE ANSWERS V2 routine ends when at Step 709 a question is encountered whose question number is 0. A branch is then made to Step 716 to set the VALIDDATA flag, after which Step 717 executes a Return From Subroutine.

In this manner, the PATHSTACK, BRANCHFLAG, NEXT/YES QUESTION POINTER, and NO QUESTION POINTER of the second embodiment enable more general branching to further questions in accordance with the patient's answers, without sacrificing the function of backup key 37. This enables the questions asked to be highly relevant and detailed with respect to the patient's age, sex, history and condition, and facilitates the asking of follow-up questions. Since the answer arrays are initialized to "NOTASKED", it is easy for the subroutines DOCREPORT and PRINTQ&A to ignore unasked questions.

The invention provides a compact, portable automatic test selector for taking patient histories which is easily used, even by bed-ridden patients, and especially adapted for the selection of medical and pre-operative tests. The test selector is easily connected to a printer to print out a report to the doctor of recommended medical and/or pre-operative tests and a sorted list of the questions and the patient's answers. It can also be attached to a suitable computerized work station. In addition, there is provision for the patient to review and supplement the answers.

While the principles of the invention have been described above in connection with specific apparatus and applications, it is to be understood that this description is intended only by way of example and not as a limitation on the scope of the invention. Therefore, the following claims are to be construed to cover all equivalent structures.

Application of Roizen, et al.

PORTABLE MEDICAL QUESTIONNAIRE PRESENTATION DEVICE

APPENDIX I

*SAMPLE*

HEALTHQUAL MD HISTORY FORM            PREOP-1.4
COPYRIGHT 1988, 1989, 1990, 1991                            JUN  6, 1991
IDENTIFICATION NUMBER : 11223344

PATIENT NAME: _____

PHYSICIAN: _____

PRESENT COMPLAINT: _____

TO THE PHYSICIAN: PLEASE VERIFY THAT THE PATIENT UNDERSTANDS
THAT THEIR ANSWERS COULD AFFECT THEIR HEALTH CARE.

The patient's answers to the        MD's COMMENTS
HealthQuiz may suggest disease       (JNS: Judged not significant
in the following systems:                 or important for this
                                          patient at this time)

SYSTEM          SYMPTOMS

HEMATOL         FORM OF ANEMIA/LEUKEMIA _____
                _____

HEMATOL         GUM BLEEDING _____
                _____

METABOLIC       THYROID DISEASE _____
                _____

METABOLIC       ARTHRITIS _____
                _____

SOME ITEMS PERTINENT TO ANESTHESIA CARE ARE:

Patient has had low back pain.
Patient has restrictions in opening mouth.
Patient has not been sleeping satisfactorily.
Patient takes medicine for thyroid disease.

CURRENT MEDS:      _____
                   _____

ALLERGIES:         _____
                   _____

PREVIOUS
OPERATIONS:        _____

HEALTHQUAL MD HIST RY FORM          PREOP-
COPYRIGHT 1988, 1.  , 1990, 1991                    JUN 6, 1991
IDENTIFICATION NUMBER : 11223344

OTHER PMH:         _____

HEIGHT:            _____

WEIGHT:            _____

VITAL SIGNS :    BP:        (Lying, Sitting, Standing)   (circle one)

HR:        RR:        T:

PE:   HEENT:       _____

LUNGS:       _____

CV:          _____

ABD:         _____

CNS:         _____

OTHER:       _____

IMP:               _____

PERTINENT
LAB TESTS:         _____

PLAN:              _____

Were risks of _____ discussed with patient?   Y or N

Were patient's questions answered?                         Y or N

Physician Signature _____

Date _____

ITEMS TO
F/U ON:            _____

```
HEALTHQUAL MD HI.  RY FORM          PREOP    4
COPYRIGHT 1988, 1989, 1990, 1991                        JUN  6, 1991
IDENTIFICATION NUMBER : 11223344
```

```
HEALTHQUAL MD HIST   FORM            PREOP-
COPYRIGHT 1988, 1989, 1990, 1991                    JUN  6, 1991
IDENTIFICATION NUMBER : 11223344

** FOR PHYSICIANS KNOWLEDGE: NOT PART OF MEDICAL RECORD **

SUGGESTED LABORATORY TESTS

CBC

If operation is associated with significant blood loss, you might
obtain Hgb or HCT.

If operation involves insertion of a prosthesis or foreign material,
you might obtain a URINALYSIS to rule out a urinary tract infection.

THE PATIENT REPORTS THAT HE/SHE HAS HAD THE FOLLOWING
TESTS RECENTLY:

Patient's stool may not have been checked for blood in the last year.
```

```
HEALTHQUAL MD HISTORY FORM           PREOP    4
COPYRIGHT 1988,   9, 1990, 1991                      JUN  6, 1991
IDENTIFICATION NUMBER : 11223344

HQSA =  6.00      HQSB = 12.50      HQSC = 15.50

ASA HS =  1.00    PATIENT ID # 11223344
```

Time required for patient to complete questionnaire:  0:03:18

Questions whose answer was marked with an asterisks:

17   18   45   64   68   93   97   98   99   110

Mkt Q   YNN

These responses to the questionnaire are meant to be an aid
to the physician. They should NOT be considered a substitute
for the physician's history, physical examination, or any
test(s) the physician deem(s) clinically indicated. Routine
performance of screening tests such as the stool guaiac or test
for occult blood in stool, Pap smears, etc. is not recommended.
Such tests may be indicated based on the physician's judgment
of their need; the above indicated laboratory tests are only
those thought appropriate for the perioperative care of this
particular patient.

** Based on the patient's response to the HealthQual
HealthQuiz, the laboratory tests above would be indicated.
These suggestions take into consideration the likelihood that
the test will uncover disease or optimize patient care versus
the risk that the test will produce a false positive result
and subsequent hazard to this patient.
   This guideline was last revised NOVEMBER 30, 1989 and is valid
to JUNE 30, 1991, and is based on data in the literature.
Such data include reviews by Roizen in Miller's ANESTHESIA,
1986 edition; by McKee and Scott in ANNALS OF THE ROYAL
COLLEGE OF SURGEONS, 1987; by Robins and Rose in MEDICAL
CLINICS OF NORTH AMERICA, 1979 and 1986; by Blery, et al. in
LANCET, January 1986; by numerous authors in ANNALS OF
INTERNAL MEDICINE  (May 1985 through December  1986),
and summarized by Sox in an American College of Physicians
Indicators for Diagnostics Tests. Similar guidelines for
radiology studies have been endorsed by an FDA panel (1984),
the American College of Surgeons, and the American College of
Physicians (not an all inclusive list). Guidelines for all
tests are similar to those presented at an NIH consensus panel
on Anesthesia for Dental Patients, endorsed in the Blue
Cross-Blue Shield Medical Necessity Guidelines, published by
the American College of Physicians in ANNALS OF INTERNAL
MEDICINE), and endorsed by the American Society of
Anesthesiology.

Application of Roizen, et al.

PORTABLE MEDICAL QUESTIONNAIRE PRESENTATION DEVICE

APPENDIX II

*SAMPLE*

```
HEALTHQUAL PATIENT RESPONSE FORM      PREOP-1.
COPYRIGHT 1988, 1989, 1990, 1991                        JUN  6, 1991
IDENTIFICATION NUMBER : 11223344
```

PATIENT NAME: _____

PHYSICIAN: _____

PRESENT COMPLAINT: _____

PLEASE REVIEW YOUR ANSWERS TO MAKE SURE THAT THEY ARE CORRECT.

### LAB TEST QUESTIONS ########

| # | Question | Answer |
|---|---|---|
| 17 | Have you ever had a problem with your blood such as anemia or leukemia? | YES ** |
| 18 | Do you bleed from your gums when you brush your teeth? | YES ** |
| 1 | Are you female? | NO |
| 5 | Are you older than 74? | NO |
| 6 | Are you older than 59? | NO |
| 7 | Are you older than 39? | NO |
| 15 | Have you ever had cancer? | NO |
| 19 | Have you ever had a blood clotting problem? | NO |
| 20 | Have you ever had a serious bleeding problem? | NO |
| 21 | Has a family member or blood relative ever had a serious bleeding problem? | NO |
| 22 | Have you ever had prolonged or unusual bleeding from cuts, nosebleeds, minor bruises, tooth extractions or surgery? | NO |
| 23 | Have you ever had excessive bleeding that required a blood transfusion? | NO |
| 25 | Have you ever had pneumonia? | NO |

```
HEALTHQUAL PATIENT  SPONSE FORM          PREOP-1
COPYRIGHT 1988, 19   1990, 1991                              JUN  6, 1991
IDENTIFICATION NUMBER : 11223344
```

| | | |
|---|---|---|
| 28 | Have you ever had a heart attack or have you been treated for a possible heart attack? | NO |
| 29 | Do you have heart problems such as skipped heart beats, angina or chest pain? | NO |
| 30 | Have you been told you have a heart murmur or rheumatic fever? | NO |
| 32 | Have you ever been told you have diabetes or sugar diabetes? | NO |
| 33 | Have you ever had a drinking problem? | NO |
| 34 | Have you ever had any problems with your kidneys, kidney failure, Dialysis or more than 2 kidney infections? | NO |
| 35 | Have you ever had kidney stones? | NO |
| 37 | Have you ever had hepatitis, yellow jaundice, liver disease or malaria? | NO |
| 38 | Have you been exposed to anyone with yellow jaundice or hepatitis within the last 6 months? | NO |
| 50 | Are your stools ever bloody or black and tarry? | NO |
| 51 | Have you vomited blood or material that looks like coffee grounds in the last 6 months? | NO |
| 53 | Have you lost weight this year without trying? | NO |
| 56 | Do you have shortness of breath, wheezing, chest pain, bronchitis, asthma or emphysema? | NO |
| 57 | Do you cough regularly or frequently? | NO |
| 58 | Do you cough up mucus (sputum or phlegm)? | NO |
| 60 | In the last 4 weeks have you had a fever, chills, cold, or flu? | NO |

HEALTHQUAL PATIENT RESPONSE FORM           PREOP-
COPYRIGHT 1988, 1989, 1990, 1991
IDENTIFICATION NUMBER : 11223344                    JUN  6, 1991

| | | |
|---|---|---|
| 61 | Have you ever woken up and felt short of breath? | NO |
| 62 | Do you become short of breath after climbing one flight of stairs or after walking a short distance? | NO |
| 65 | Do you have muscle cramps or spasms in your legs more than 3 times a YEAR? | NO |
| 66 | Do you have any pain or discomfort with urination, or have you noticed blood in your urine? | NO |
| 76 | Have you received a blood transfusion in the last 6 MONTHS? | NO |
| 77 | Have you received a blood transfusion since 1979? | NO |
| 78 | Have you been told by your doctor to exercise or diet to control high blood pressure? | NO |
| 79 | Have you had blood tests in the last 6 MONTHS? | NO |
| 80 | Have you had a chest x-ray in the last 2 MONTHS? | NO |
| 81 | Have you had an EKG (an electrocardiogram) in the last 2 MONTHS? | NO |
| 82 | Has your stool been checked for blood in the last YEAR? | NO |
| 87 | Have you ever smoked half a pack or more of cigarettes a day on a regular basis? | NO |
| 92 | Do you sleep with more than one pillow at night? | NO |
| 100 | Have you had a drink of beer, wine, or liquor or any drink containing alcohol in the last 24 HOURS? | NO |
| 101 | Within the last 2 YEARS have you taken non-prescription drugs like cocaine, crack, heroin or LSD? | NO |

```
HEALTHQUAL PATIEN  ESPONSE FORM        PREOP-
COPYRIGHT 1988, 1989, 1990, 1991                        JUN  6, 1991
IDENTIFICATION NUMBER : 11223344
```

| | | |
|---|---|---|
| 102 | Have you been exposed to the body fluids (blood, semen, urine, saliva) or anyone likely to have the AIDS virus? | NO |
| 103 | Are you in a high risk group for AIDS? (gay, bisexual, hemophiliac, or had sex with a prostitute in the last 6 YEARS?) | NO |
| 104 | Would you like to receive a test to find out if you have been exposed to the AIDS virus? | NO |
| 108 | Have you taken Aspirin, Excedrin, Anacin, Bufferin, Alka Seltzer or any similar medications containing aspirin in the last 2 WEEKS? | NO |
| 114 | Do you currently take drugs to suppress your immune system such as Cyclosporin, Azathioprine, Imuran, Cyclophosphamide, or 6-mercaptopurine? | NO |
| 115 | Do you currently take heart medication such as Inderal (Propranolol), Tenormin, Verapamil, Nifedipine, Diltiazem, Quinidine or ACE inhibitors? | NO |
| 116 | Do you currently take heart medication such as Digoxin, Digitoxin, Digitalis Hydralazine (Apresolin), Nitroglycerine Captopril (Capoten) or Lanoxin? | NO |
| 118 | Do you currently take any medication for high blood pressure? | NO |
| 119 | Do you currently take water pills or diuretics? | NO |
| 120 | Do you currently take potassium pills or powder? | NO |
| 121 | Do you currently take anticoagulants or blood thinning medicine? | NO |
| 127 | Do you currently take heart medication or antiarrhythmics such as Procainamide, Quinidine, or Disopyramide (Norpace)? | NO |
| 129 | Have you ever been told that you had Diphtheria? | NO |

```
HEALTHQUAL PATIEN  ESPONSE FORM          PREOP-
COPYRIGHT 1988, 1989, 1990, 1991                        JUN  6, 1991
IDENTIFICATION NUMBER : 11223344
```

135                                                     NO
    Are you older than 64?

136                                                     NO
    Are you older than 49?

137  Do you use or have you ever used         NO
    smokeless tobacco (for example,
    snuff or chewing tobacco)?

\*\*\*\*\*\*\* ANESTHESIA QUESTIONS \*\*\*\*\*\*\*

68  Do you have, or have you had            YES  \*\*
    low back pain?

8  Do you wear dentures, a crown,            NO
    a partial or a bridge?

9  Do you have any capped teeth?             NO

10  Are any of your teeth loose,             NO
    cracked, or chipped?

11  Do you wear contact lenses?              NO

12  Have you had Anesthesia in the past?     NO

13  Have you or any blood relative           NO
    ever had any
    problems with Anesthesia?

24  Do you have any allergies?               NO

39  Have you ever had gallstones or          NO
    gallbladder disease?

45  Can you open your mouth fully?           NO  \*\*

46  Do you have any clicking, popping,       NO
    or pain in your
    jaw joints?

47  Have you ever been treated for a         NO
    jaw joint problem (TMJ or
    temporomandibular jaw joint problem)?

48  Have you ever had heart or               NO
    lung surgery?

69  Do you have neck stiffness or            NO
    problems moving your head?

HEALTHQUAL PATIENT RESPONSE FORM     PREOP-
COPYRIGHT 1988, 1989, 1990, 1991
IDENTIFICATION NUMBER : 11223344            JUN 6, 1991

| | | |
|---|---|---|
| 83 | Have you been a patient in a hospital, emergency room, or outpatient surgery center in the last 2 YEARS? | NO |
| 111 | Have you taken antidepressants, sedatives or tranquilizers in the last YEAR? | NO |
| 112 | Have you taken pain pills, or had pain shots in the last 6 MONTHS? | NO |
| 113 | Do you take or have you taken steroids, cortisone, or ACTH in the last year? | NO |
| 117 | Do you currently use eye drops other than Visine or Murine? | NO |
| 122 | Have you ever been told to take or been given antibiotics before routine dental work? | NO |
| 131 | Have you ever been hoarse for over 1 month? | NO |
| 132 | Have you ever been treated for or had arthritis? | NO |
| 134 | Do you perspire (sweat) much more than others or a great deal every now and then? | NO |

**** GENERAL HEALTH QUESTIONS ***

| | | |
|---|---|---|
| 54 | Are you eating the same foods you ate a year ago? | YES |
| 110 | Are you taking (or did you ever take) medicine for thyroid disease (for example, Synthroid or I-131)? | YES ** |
| 124 | Did you understand all of the HealthQuiz questions? | YES |
| 27 | Have you been diagnosed as having a hiatus hernia? | NO |
| 31 | Have you ever been told that you have mitral valve prolapse? | NO |

HEALTHQUAL PATIENT RESPONSE FORM     PREOP-1
COPYRIGHT 1988, 1.   , 1990, 1991                          JUN  6, 1991
IDENTIFICATION NUMBER : 11223344

| | | | |
|---|---|---|---|
| 36 | Are you being Dialyzed for kidney problems? | NO | |
| 40 | Have your bowel or bladder functions changed in the last YEAR? | NO | |
| 41 | Have you ever had a seizure, convulsion, fit, stroke or been paralyzed? | NO | |
| 42 | Have you ever been diagnosed as having a tremor? | NO | |
| 43 | Do you have, or have you ever had migraine headaches? | NO | |
| 44 | Have you ever had nerve injuries, multiple sclerosis or any nervous system disorders? | NO | |
| 52 | Has your appetite for food changed in the last year? | NO | |
| 55 | Have you had heartburn within the last MONTH? | NO | |
| 63 | Do your ankles ever swell? | NO | |
| 64 | Are you able to walk up stairs at the same rate you could 5 years ago? | NO | ** |
| 67 | Have you ever had numbness, tingling or pins and needles in your arm or leg lasting more than 2 hours? | NO | |
| 70 | Are you ever short of breath? | NO | |
| 72 | Do you ever have chest pains, angina, chest heaviness, or chest tightness? | NO | |
| 74 | Do you ever have indigestion NOT associated with over-eating? | NO | |
| 86 | Have you ever smoked a pipe or cigars on a regular basis? | NO | |
| 93 | Have you been sleeping OK in the last 2 WEEKS? | NO | ** |
| 97 | Have you been working your usual job or doing your normal activities in the last WEEK? | NO | ** |

```
HEALTHQUAL PATIENT  SPONSE FORM         PREOP-1
COPYRIGHT 1988, 1989, 1990, 1991                            JUN  6, 1991
IDENTIFICATION NUMBER : 11223344
```

98   Have you engaged in any                   NO  **
       hobbies
       in the last 2 WEEKS?

99   Have you been able to eat, wash,        NO  **
       dress and walk
       by yourself in the last 2 WEEKS?

106   Have you taken Tylenol,                 NO
       or any other acetaminophen
       in the last WEEK?

107   Have you taken any Advil, Nuprin,       NO
       Metaprin, Motrin or other
       ibuprofen
       in the last WEEK?

109   Are you currently taking antacids,      NO
       or Tagamet (Cimetidine)
       Zantac (Ranitidine) Pepsid, or Axid?

123   Do you take any medicines not asked     NO
       about?

125   Did you require help                    NO
       to answer the HealthQuiz questions?

126   Did you find the HealthQuiz            NO
       somewhat
       difficult to use?

The above answers are correct as typed.

Patient
Signature _____  Date _____

What is claimed is:

1. For use with a hand-held medical-history-taking device, the method of reporting which particular anatomical systems, among a plurality of candidate anatomical systems, are associated with at least one health symptom, responsive to information supplied by the patient, comprising the steps of:

(a) providing question storage means in said history-taking device storing a plurality of questions to be asked of a medical patient;

(b) providing answer storage means in said history-taking device for storing a plurality of answers obtained from said patient and respectively associated with said questions;

(c) providing, first list storage means in said history-taking device storing a first list identifying, for each of said plurality of candidate anatomical systems, at least one of said symptoms as being associated with said anatomical system;

(d) providing second list storage means in said history-taking device storing a second list identifying, for each of said health symptoms, at least one of said questions as being associated with said health symptom;

(e) causing said history-taking device to consult said question storage means to present a selected sequence of said questions to said patient, causing said history-taking device to solicit a respective answer to each of said questions of said sequence, and causing said history-taking device to store each of said answers in said answer storage means;

(f) causing said history-taking device to select, in turn, each of said plurality of candidate anatomical systems, and causing said history-taking device to consult said first list storage means to determine which health symptoms are associated with said selected anatomical system;

(g) causing said history-taking device to select, in turn, each of said health symptoms determined in the previous step, and causing said history-taking device to consult said second list storage means to determine which questions are associated with said selected health symptom;

(h) causing said history-taking device to select, in turn, each of said questions determined in the previous step, and causing said history-taking device to consult said answer storage means to determine whether the stored answer associated with that question is non-negative; and (i) if said stored answer is non-negative, causing said history-taking device to produce printer signals to cause an external printer to present in a printed report a report element associating said selected anatomical system with said selected health symptom.

2. The method of claim 1 wherein said step (h) of causing said history-taking device to consult said answer storage means further comprises the steps of:

causing said history-taking device to retrieve said stored answer; and causing said history-taking device to determine that said stored answer is non-negative if said stored answer corresponds to "Yes" or "Not Sure".

3. The method of claim 1 further comprising the step of:

(j) once a non-negative response to any question associated with said selected health symptom has caused a report element associating said selected anatomical system with said selected health symptom to be presented, causing said history-taking device to inhibit further selection of questions associated with the selected health symptom and instead to select in turn a next available health symptom which is associated with said selected anatomical system.

4. For use with a hand-held medical-history-taking device, the method of reporting which particular members of a first subject-matter category among a plurality of candidate members of said first subject matter category, are associated with at least one member of a second subject matter category, at least one of said subject matter categories diagnostically indicated by information supplied by the patient, comprising the steps of:

(a) providing question storage means in said history-taking device storing a plurality of questions to be asked of a medical patient;

(b) providing answer storage means in said history-taking device for storing a plurality of answers obtained from said patient and respectively associated with said questions;

(c) providing first list storage means in said history-taking device storing a first list identifying, for each of said plurality of candidate members of said first subject-matter category, at least one member of said second subject-matter category as being associated with said member of said first subject-matter category;

(d) providing second list storage means in said history-taking device storing a second list identifying, for each of said members of said second subject matter category, at least one of said questions as being associated with said member of said second subject-matter category;

(e) causing said history-taking device to consult said question storage means to present a selected sequence of said questions to said patient, causing said history-taking device to solicit a respective answer to each of said questions of said sequence, and causing said history-taking device to store each of said answers in said answer storage means;

(f) causing said history-taking device to select, in turn, each of said plurality of members of said first subject-matter category, and causing said history-taking device to consult said first list storage means to determine which members of said second subject-matter category are associated with said selected member of said first subject-matter category;

(g) causing said history-taking device to select, in turn, each of said members of second subject-matter category determined in the previous step, and causing said history-taking device to consult said second list storage means to determine which questions are associated with said selected member of said second subject-matter category;

(h) causing said history-taking device to select, in turn, each of said questions determined in the previous step, and causing said history-taking device to consult said answer storage means to determine whether the stored answer associated with that question is non-negative; and (i) if said stored answer is non-negative, causing said history-taking device to produce printer signals to cause an external printer to present in a printed report a report element associating said selected member of said first subject-matter category with said selected member of said second subject-matter category.

5. A hand-held medical-history-taking device adapted for reporting which particular anatomical systems, among a plurality of candidate anatomical systems, are associated with at least one health symptom, responsive to information supplied by the patient, comprising:

(a) question storage means storing a plurality of questions to be asked of a medical patient;

(b) answer storage means for storing a plurality of answers obtained from said patient and respectively associated with said questions;

(c) first list storage means storing a first list identifying, for each of said plurality of candidate anatomical systems, at least one of said health symptoms as being associated with said anatomical system;

(d) second list storage means storing a second list identifying, for each of said health symptoms, at least one of said questions as being associated with said health symptom;

(e) means for consulting said question storage means to present a selected sequence of said questions to said patient, soliciting a respective answer to each of said questions of said sequence, and storing each of said answers in said answer storage means;

(f) means for selecting, in turn, each of said plurality of candidate anatomical systems, and consulting said first list storage means to determine which health symptoms are associated with said selected anatomical system;

(g) means for selecting, in turn, each of said health symptoms determined to be associated with said selected anatomical system, and consulting said second list storage means to determine which questions are associated with said selected health symptom;

(h) means for selecting, in turn, each of said questions determined determined to be associated with said selected health symptom, and consulting said answer storage means to determine whether the stored answer associated with that question is non-negative; and (i) means for producing printer signals to cause an external printer to present in a printed report a report element associating said selected anatomical system with said selected health symptom, if said stored answer is non-negative.

6. The apparatus of claim 5 wherein said means (e) for consulting said answer storage means further comprises:

means for retrieving said stored answer; and means for determining that said stored answer is non-negative if said stored answer corresponds to "Yes" or "Not Sure".

7. The apparatus of claim 5 further comprising:

(j) means for inhibiting further selection of questions associated with the selected health symptom and instead selecting in turn a next available health symptom which is associated with said selected anatomical system, once a non-negative response to any question associated with said selected health symptom has caused a report element associating said selected anatomical system with said selected health symptom to be presented.

8. A hand-held medical history-taking device adapted for reporting which particular members of a first subject-matter category, among a plurality of members of said first subject matter category, are associated with at least one member of a second subject matter category, at least one of said subject matter categories diagnostically indicated by information supplied by the patient, comprising:

(a) question storage means storing a plurality of questions to be asked of a medical patient;

(b) answer storage means for storing a plurality of answers obtained from said patient and respectively associated with said questions;

(c) first list storage means storing a first list identifying, for each of said plurality of candidate members of said first subject-matter category, at least one member of said second subject-matter category as being associated with said member of said first subject-matter category;

(d) second list storage means storing a second list identifying, for each of said members of said second subject matter category, at least one of said questions as being associated with said member of said second subject-matter category;

(e) means for consulting said question storage means to present a selected sequence of said questions to said patient, soliciting a respective answer to each of said questions of said sequence, and storing each of said answers in said answer storage means;

(f) means for selecting, in turn, each of said plurality of members of said first subject-matter category, and said first list storage means to determine which members of said second subject-matter category are associated with said selected member of said first subject-matter category;

(g) means for selecting, in turn, each of said members of second subject-matter category determined to be be associated with said selected member of said first subject matter category, and consulting said second list storage means to determine which questions are associated with said selected member of said second subject-matter category;

(h) means for selecting each of said questions determined to be associated with said selected member of said second subject matter category, and consulting said answer storage means to determine whether the stored answer associated with that question is non-negative; and (i) means for producing printer signals to cause an external printer to present in a printed report a report element associating said selected member of said first subject-matter category with said selected member of said second subject-matter category, if said stored answer is non-negative.

* * * * *